US008156932B2

(12) United States Patent
Lee

(10) Patent No.: US 8,156,932 B2
(45) Date of Patent: Apr. 17, 2012

(54) METHOD AND APPARATUS TO RELIEVE MENSTRUAL PAIN

(75) Inventor: Stephen D. Lee, Sarasoto, FL (US)

(73) Assignee: Embrace LLC, Sarasota, FL (US)

( * ) Notice: Subject to any disclaimer, the term of this patent is extended or adjusted under 35 U.S.C. 154(b) by 348 days.

(21) Appl. No.: 12/404,655

(22) Filed: Mar. 16, 2009

(65) Prior Publication Data
US 2009/0173340 A1 Jul. 9, 2009

Related U.S. Application Data

(63) Continuation-in-part of application No. 11/753,562, filed on May 24, 2007, now abandoned.

(51) Int. Cl.
A61F 5/28 (2006.01)
A61F 5/30 (2006.01)
A61F 5/24 (2006.01)

(52) U.S. Cl. ............... 128/99.1; 128/102.1; 128/106.1; 128/115.1; 128/121.1

(58) Field of Classification Search .............. 128/95.1, 128/96.1, 100.1, 103.1, 108.1, 99.1, 106.1; 128/118.1, 102.1, 115.1, 121.1; 602/19; 450/134; 607/108, 112
See application file for complete search history.

(56) References Cited

U.S. PATENT DOCUMENTS

| 35,038 | A |  | 4/1862 | Pierce |  |
|---|---|---|---|---|---|
| 1,600,178 | A |  | 9/1926 | Hussey |  |
| 2,018,981 | A |  | 10/1935 | Tietjen |  |
| D99,529 | S |  | 5/1936 | Spanel |  |
| D134,791 | S |  | 1/1943 | Selver |  |
| 2,453,370 | A |  | 11/1948 | Hittenberger |  |
| 2,493,406 | A |  | 1/1950 | Hicks |  |
| 2,497,443 | A | * | 2/1950 | Eatman | ............... 607/108 |
| 2,552,475 | A |  | 5/1951 | Austlid |  |
| 2,590,212 | A |  | 3/1952 | Samuels |  |
| 2,644,449 | A |  | 7/1953 | Champagne |  |
| 2,652,051 | A |  | 9/1953 | Hoover |  |
| 2,654,366 | A |  | 10/1953 | Miller |  |
| 2,813,526 | A |  | 11/1957 | Beebe |  |
| 2,828,737 | A |  | 4/1958 | Hale |  |
| 3,071,133 | A |  | 1/1963 | Eisen |  |
| 3,351,053 | A |  | 11/1967 | Stuttle |  |
| 3,393,674 | A |  | 7/1968 | Schaffer |  |
| 3,396,264 | A |  | 8/1968 | Murphy et al. |  |
| 3,500,014 | A |  | 3/1970 | Longo |  |
| 3,501,616 | A |  | 3/1970 | Arron |  |
| 3,518,995 | A |  | 7/1970 | Claff |  |
| 3,532,090 | A | * | 10/1970 | Ward et al. | ............... 128/121.1 |
| 3,548,817 | A |  | 12/1970 | Mittach |  |

(Continued)

Primary Examiner — Patricia Bianco
Assistant Examiner — Ophelia Hawthorne
(74) Attorney, Agent, or Firm — Allen, Dyer, Doppelt, Milbrath & Gilchrist, P.A.

(57) ABSTRACT

An apparatus to relieve menstrual cramping which includes one or more symmetrical tapered pads having an inner and outer side, each outer side being semi-rigid and each inner side being flexible and compressible. The outer side of each pad is connected to one or more straps having a first and corresponding second end. A fastener is attached to the first end of each strap and a corresponding second fastener attaches to the second end of each strap. The apparatus also includes a constricting device (such as a ratchet) located on or proximate to one pad sufficient to create a compression force through each strap when the first and corresponding second fasteners connect to one another. The corresponding method includes the steps of placing one or more pads proximate to the hips, affixing each pad to each strap, connecting both ends of the straps to each other and creating necessary compression.

14 Claims, 24 Drawing Sheets

U.S. PATENT DOCUMENTS

| | | |
|---|---|---|
| 3,577,986 A | 5/1971 | Regent |
| 3,680,563 A | 8/1972 | Forrest |
| 3,797,501 A | 3/1974 | Di Tullio |
| 4,122,552 A | 10/1978 | Tedford |
| D258,770 S | 4/1981 | Stern |
| 4,577,622 A | 3/1986 | Jennings |
| 4,580,555 A | 4/1986 | Coppess |
| 4,622,957 A | 11/1986 | Curlee |
| 4,671,264 A | 6/1987 | Frangi |
| 4,675,918 A | 6/1987 | O'Brien |
| 4,681,113 A | 7/1987 | Coplans |
| 4,715,364 A | 12/1987 | Noguchi |
| 4,761,834 A * | 8/1988 | Kolb ................................ 2/465 |
| 4,905,678 A * | 3/1990 | Cumins et al. .................. 602/16 |
| 4,912,813 A | 4/1990 | Muller et al. |
| 4,937,887 A | 7/1990 | Schreiner |
| 4,957,105 A | 9/1990 | Kurth |
| 4,993,409 A | 2/1991 | Grim |
| 5,129,647 A | 7/1992 | Castellanos |
| 5,363,863 A | 11/1994 | Lelli et al. |
| 5,383,893 A | 1/1995 | Daneshvar |
| 5,383,920 A | 1/1995 | Sikes |
| 5,388,274 A | 2/1995 | Glover et al. |
| 5,407,422 A | 4/1995 | Matthijs et al. |
| 5,437,618 A | 8/1995 | Sikes |
| 5,476,492 A | 12/1995 | Unrug |
| 5,486,680 A | 1/1996 | Lieberman |
| 5,528,775 A | 6/1996 | Marenda |
| 5,551,093 A | 9/1996 | Stricker |
| 5,588,186 A | 12/1996 | Ko |
| 5,628,721 A | 5/1997 | Arnold et al. |
| D380,051 S | 6/1997 | Davis et al. |
| 5,647,824 A | 7/1997 | Levenson |
| 5,690,122 A | 11/1997 | Weber-Unger |
| 5,728,055 A | 3/1998 | Sebastian |
| 5,782,781 A | 7/1998 | Nagaoka |
| 5,799,650 A | 9/1998 | Harris |
| 5,817,145 A | 10/1998 | Augustine et al. |
| 5,830,168 A | 11/1998 | Finnell et al. |
| 5,893,368 A | 4/1999 | Sugerman |
| 5,913,410 A | 6/1999 | Tsuchiya |
| 5,947,914 A | 9/1999 | Augustine |
| 5,954,680 A | 9/1999 | Augustine |
| 5,964,721 A | 10/1999 | Augustine |
| 5,964,723 A | 10/1999 | Augustine |
| 5,986,163 A | 11/1999 | Augustine |
| 6,010,527 A | 1/2000 | Augustine et al. |
| 6,013,097 A | 1/2000 | Augustine et al. |
| 6,045,518 A | 4/2000 | Augustine |
| 6,065,166 A | 5/2000 | Sharrock et al. |
| 6,066,109 A * | 5/2000 | Buser et al. ..................... 602/23 |
| 6,071,254 A | 6/2000 | Augustine |
| 6,093,160 A | 7/2000 | Augustine et al. |
| 6,099,490 A | 8/2000 | Turtzo |
| 6,110,197 A | 8/2000 | Augustine et al. |
| 6,213,966 B1 | 4/2001 | Augustine |
| 6,217,535 B1 | 4/2001 | Augustine |
| 6,235,049 B1 | 5/2001 | Nazerian |
| 6,241,697 B1 | 6/2001 | Augustine |
| 6,241,698 B1 | 6/2001 | Augustine |
| 6,248,084 B1 | 6/2001 | Augustine et al. |
| 6,264,622 B1 | 7/2001 | Augustine |
| 6,267,740 B1 | 7/2001 | Augustine et al. |
| 6,293,917 B1 | 9/2001 | Augustine et al. |
| 6,328,627 B1 | 12/2001 | Smith |
| 6,406,448 B1 | 6/2002 | Augustine |
| 6,407,307 B1 | 6/2002 | Augustine |
| 6,419,651 B1 | 7/2002 | Augustine |
| 6,423,018 B1 | 7/2002 | Augustine |
| 6,460,195 B2 | 10/2002 | Wang |
| 6,465,708 B1 | 10/2002 | Augustine |
| 6,468,295 B2 | 10/2002 | Augustine et al. |
| 6,580,012 B1 | 6/2003 | Augustine et al. |
| 6,592,428 B2 | 7/2003 | Smith |
| 6,605,051 B2 | 8/2003 | Augustine |
| 6,613,034 B2 | 9/2003 | Nozaki et al. |
| 6,634,533 B2 | 10/2003 | Thompson et al. |
| 6,820,574 B2 | 11/2004 | Sharpe |
| 6,840,915 B2 | 1/2005 | Augustine |
| 6,921,374 B2 | 7/2005 | Augustine |
| 6,987,209 B2 | 1/2006 | Augustine et al. |
| 7,008,389 B2 | 3/2006 | Krieg et al. |
| 7,066,181 B2 | 6/2006 | West |
| 7,122,046 B2 | 10/2006 | Augustine et al. |
| 7,824,437 B1 * | 11/2010 | Saunders ..................... 607/108 |

* cited by examiner

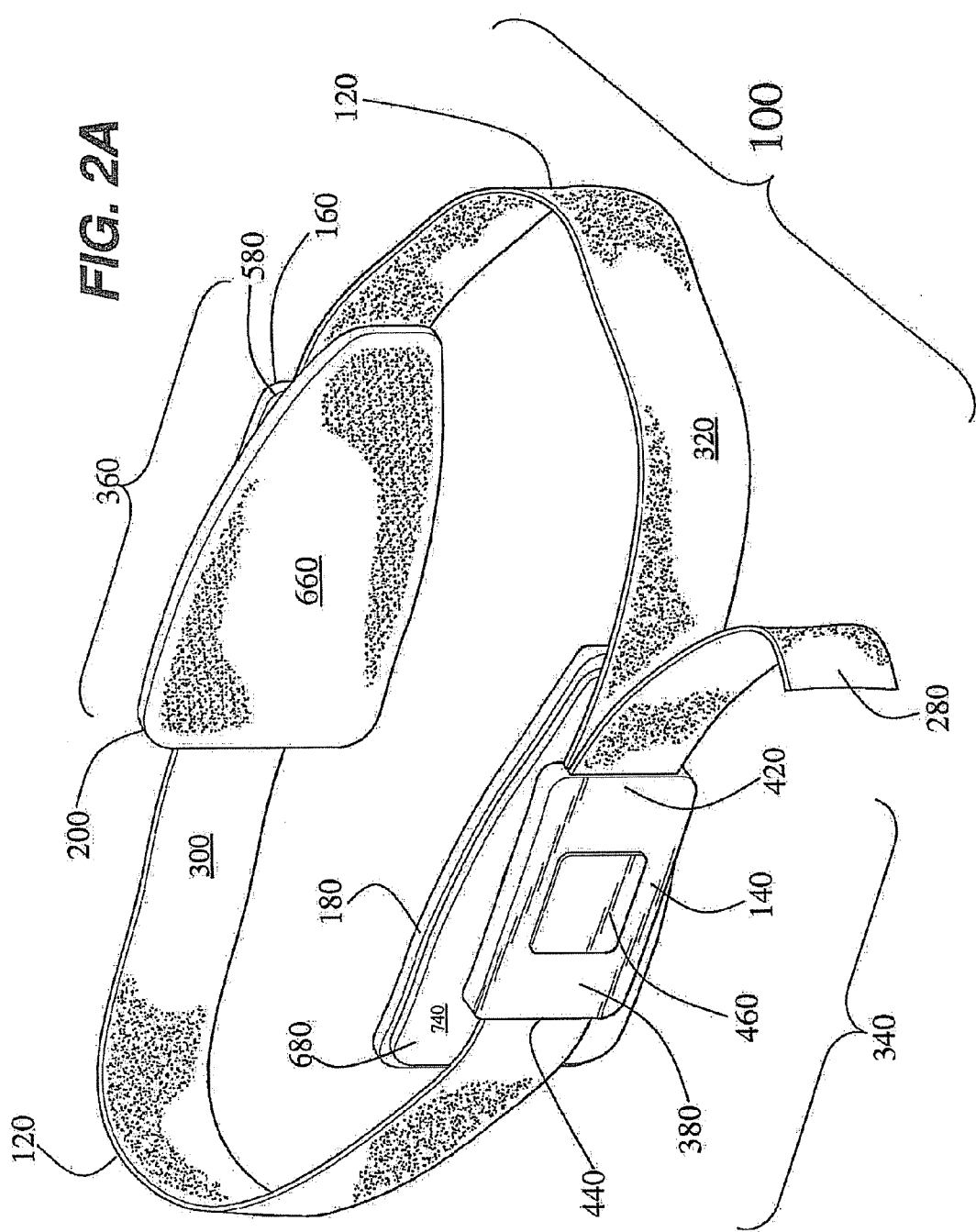

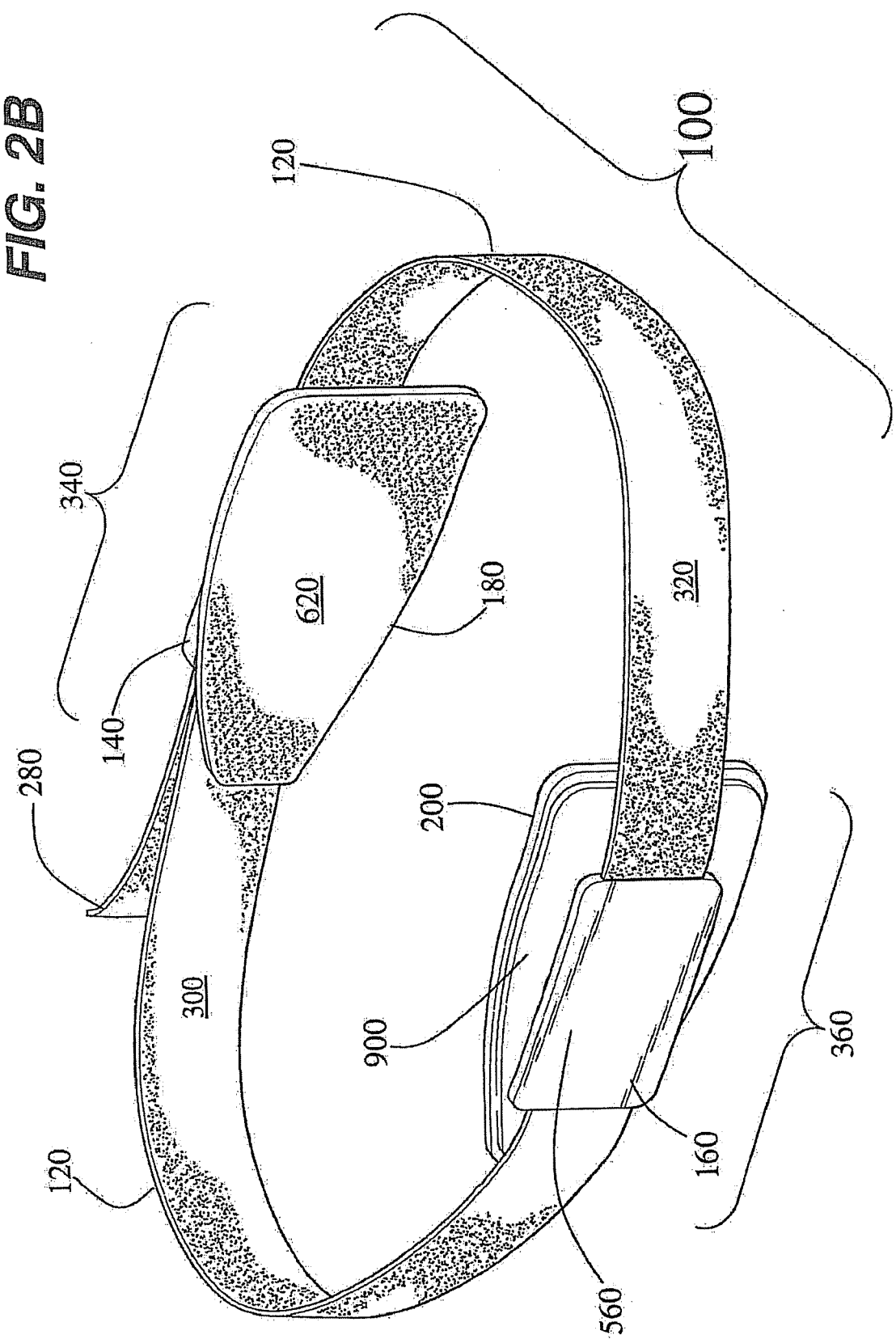

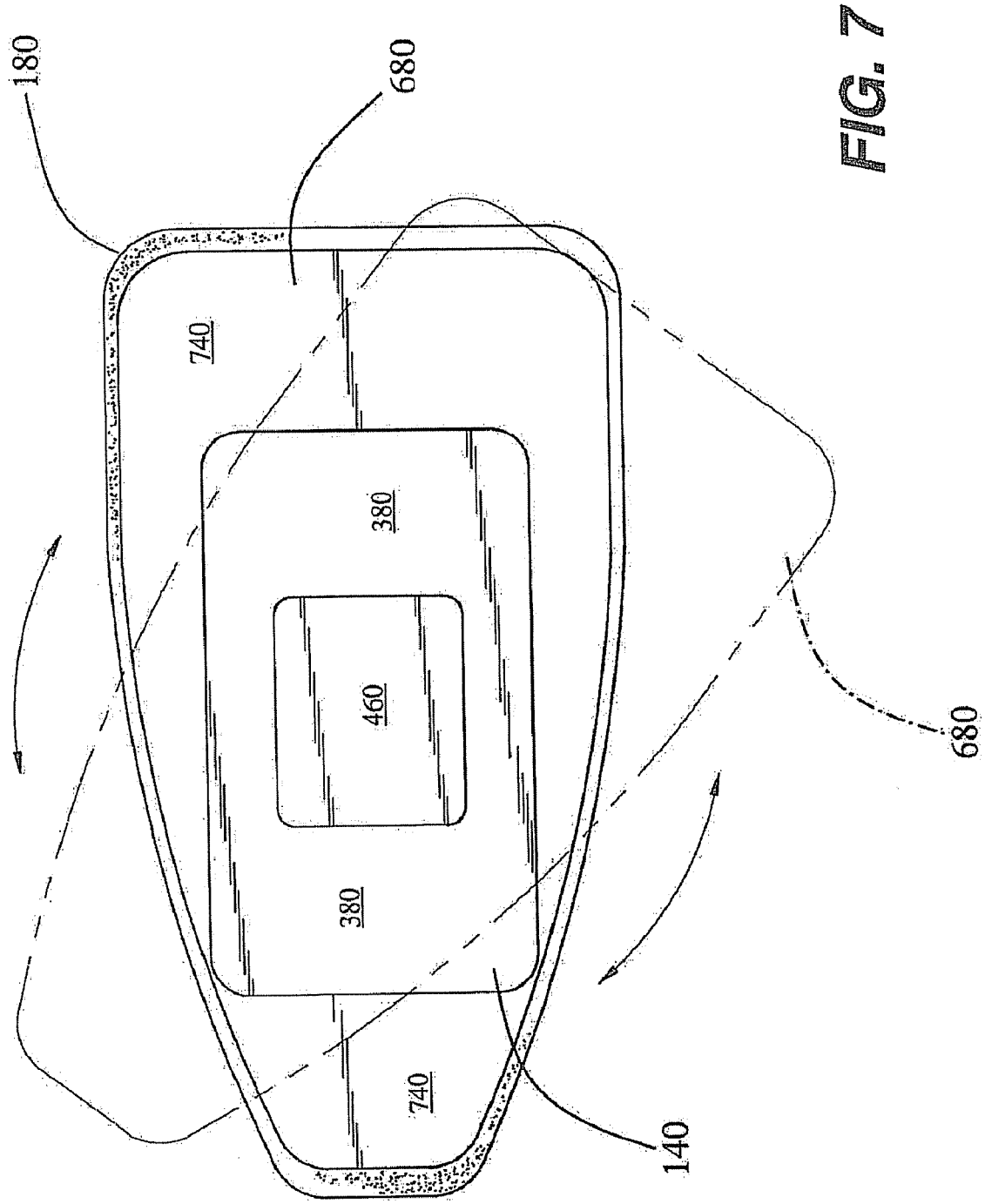

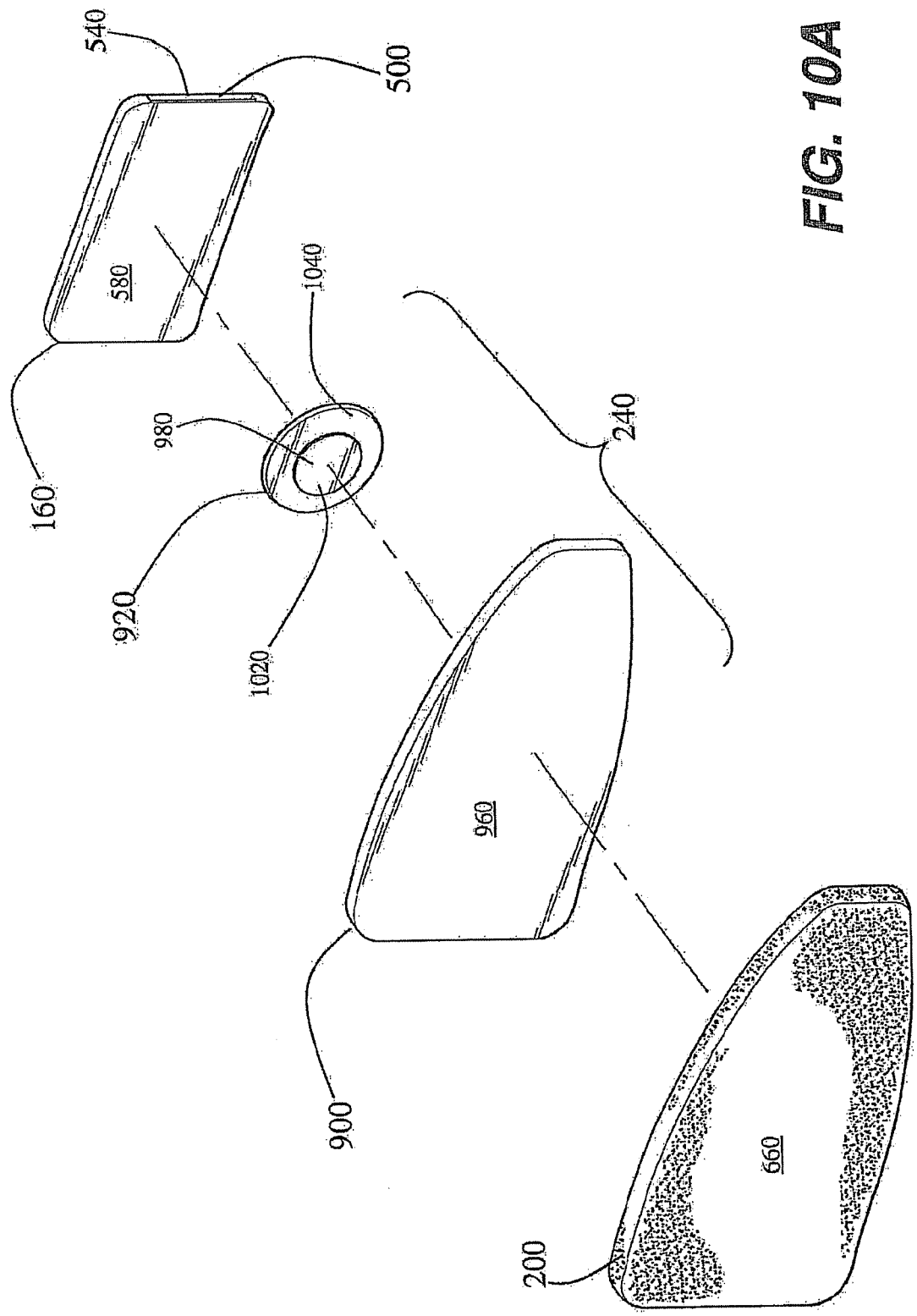

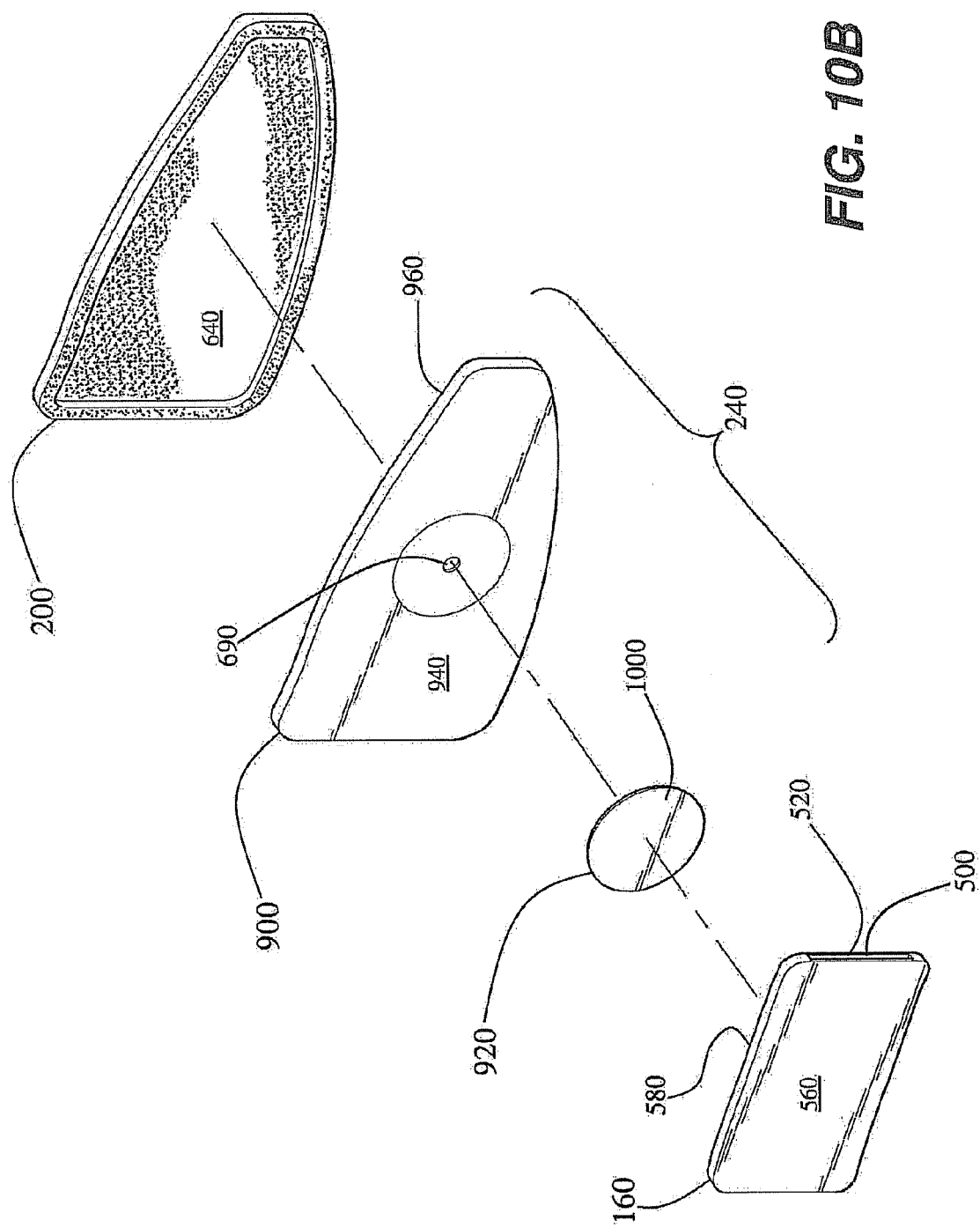

METHOD AND APPARATUS TO RELIEVE MENSTRUAL PAIN

CROSS-REFERENCE TO RELATED APPLICATIONS

This is a continuation-in-part of application Ser. No. 11/753,562 filed on May 24, 2007, which is incorporated by reference herein.

STATEMENT REGARDING FEDERALLY SPONSORED RESEARCH OR DEVELOPMENT

Not Applicable.

FIELD OF THE INVENTION

The present invention relates to a method and apparatus to relieve menstrual pain. More specifically, the invention relates to a method and apparatus to relieve menstrual cramping through applying pressure to the exterior of the female body proximate to the hips.

BACKGROUND OF INVENTION

Menstrual cramping (dysmenorrheal) is a medical condition characterized by severe uterine pain during menstruation. The condition is the result of contractions of the uterus as it expels unneeded contents and also the passage of clotted blood through the cervix. The underlying pain results when the uterine muscles contract too hard or fast resulting in severe discomfort around the abdomen, back and often the legs.

The condition most commonly affects women between the ages of 20 through 24. While most women only experience minor pain during menstruation, menstrual cramps are often so severe as to limit normal activities or may require medication. Menstrual cramping may precede menstruation by several days or may accompany it. More typically, such cramping occurs on the first or second day of the menstrual cycle.

According to the United States Department of Health and Human Services, roughly 52 percent of women in the United States between the ages of 15 to 51 suffer from some level of menstrual cramps. Of these, 10 percent have such a severe condition as to require a doctor visit. Statistics from the American College of Obstetrics and Gynecology reveal that menstrual cramping represents the number one cause of missed school and work days among women. In fact, menstrual cramping accounts for an astonishing 140 million hours of lost school and work every year.

Despite these alarming statistics, very little has been done to advance the art of treating menstrual cramping. Traditional methods of chemical treatment include taking an over-the-counter pain killer which includes ibuprofen as the active ingredient. Non-traditional methods include a regiment of taking calcium, Vitamin D and magnesium supplements. Non-medicinal ways of treatment typically include use of heat around the abdomen, such as a heating pad or taking a warm sitz-bath.

Each aforementioned treatment option has its limitations, and none actually work to treat the underlying medical cause of these cramps. Studies show how increased ingestion of ibuprofen may result in multiple adverse drug reactions (ADRs), as well as associated gastrointestinal (GI) effects and renal problems. Many women cannot always take chemical medications due to these problems as well as other undesirable side affects. Dietary supplements like calcium, Vitamin D and magnesium may help reduce pain but do not eliminate or treat the condition. Use of heat around the abdomen only offers at most temporary relief and does nothing more than mask the pain.

With the growing acceptance of complementary and alternative medicine (CAD), there is a need in the art for an effective yet non-chemical treatment of menstrual cramps. This is especially true with the large number of individuals whose personal and spiritual beliefs preclude use of chemical medicines like ibuprofen.

SUMMARY OF THE INVENTION

This invention solves the current limitations in the art of alleviating menstrual cramps through an alternative and non-chemical form of treatment. As menstrual cramping occurs when the uterine muscles contract too hard or fast resulting in the various tissue connected to (or located near) the uterus to expand, the present invention treats the condition through counteracting this excessive stretching. Specifically, to relieve the pain and discomfort associated with menstrual cramping, the invention employs compression at or proximate to each greater trochater—the large, irregular eminence located at the top of the femur bone—at both lateral sides of the female hips. Through compressing the area adjacent to each greater trochanter, the ligaments and tendons proximate to the uterus relax, helping alleviate menstrual cramps and associated pain.

In the preferred embodiment, the apparatus includes one or more symmetrical tapered pads having an inner side and an outer side. Each outer side of each pad is semi-rigid while each inner side is flexible and compressible. The outer side of each pad is connected to one or more straps, each strap having a first end and a corresponding second end. A fastener is attached to the first end of each strap and a corresponding second fastener is attached to the second end of each strap. Both fasteners can be a buckle system, a latch system, Velcro or any other related locking system known in the art. In addition, a constricting device is located on or proximate to one pad sufficient to create a compression force through each strap when the first fastener and corresponding second fastener are connected to one another. Such constricting device may be a ratchet, pulley system or similar device known in the art.

In a second embodiment of the apparatus, the symmetrically tapered pads are attached to one or more straps through a swivel bracket in order to vertically rotate the pad to conform with the user's hips.

In a third embodiment of the apparatus, an inner bladder system supplants the flexible and compressible inner side of the pads. The inner bladder can be filled with a gas or liquid sufficient to conform to the user's hips.

In a fourth embodiment, the apparatus has one or more symmetrically tapered pads, each having an outer side and an inner side. The outer side of each pad is affixed to the inner side of a C-shaped belt. In addition, the C-shaped belt has a constricting device, which can include, but is not necessarily limited to, a spring-member (and/or screw based system attached to each pad) sufficient to compress each symmetrically tapered pad onto the greater trochanters of the user.

The inner portion of each aforementioned tapered pads can be made of any material which can be warmed to allow the benefits of heat to further treat menstrual pain.

The preferred embodiment of the method includes the steps of placing one or more pads proximate to the greater trochanters of a user; affixing each pad to one or more straps where each strap has a first end and a second end at the opposite portion of each strap; connecting the first and second end of each strap through a fastener, and creating pressure sufficient to compress each said pad onto said user. Under this preferred method, 10 to 15 pounds of pressure is administered for between 5 to 10 minutes after the user reports the menstrual pain has subsided.

The method can also include the additional steps of shaping each pad to conform with the shape of the user's hip(s), as well as vertically rotating each pad through a swivel bracket into a position which further conforms with the shape of each hip. The systems and methods described herein are meant to not only treat menstrual cramping but also to provide relief from more minor episodes of menstrual pain and discomfort.

BRIEF DESCRIPTION OF THE DRAWINGS

FIG. 2A shows a left perspective view of the apparatus.

FIG. 2B shows a right perspective view of the apparatus.

FIG. 7 shows a perspective view of the left pad of the apparatus showing how the left pad can be rotated.

FIG. 10A shows an exploded view of the right part of the apparatus.

FIG. 10B shows a further exploded view of the right part of the apparatus.

FIG. 13(a) shows a ratchet system, while FIG. 13(b) shows a pulley system.

FIG. 14(a) is an exploded view of a two-part construction having a semi-rigid outer side and a flexible and compressible inner side. FIG. 14(b) shows the two-part construction having a semi-rigid outer side and a inner bladder system.

DETAILED DESCRIPTION OF THE INVENTION

Figure 1A:
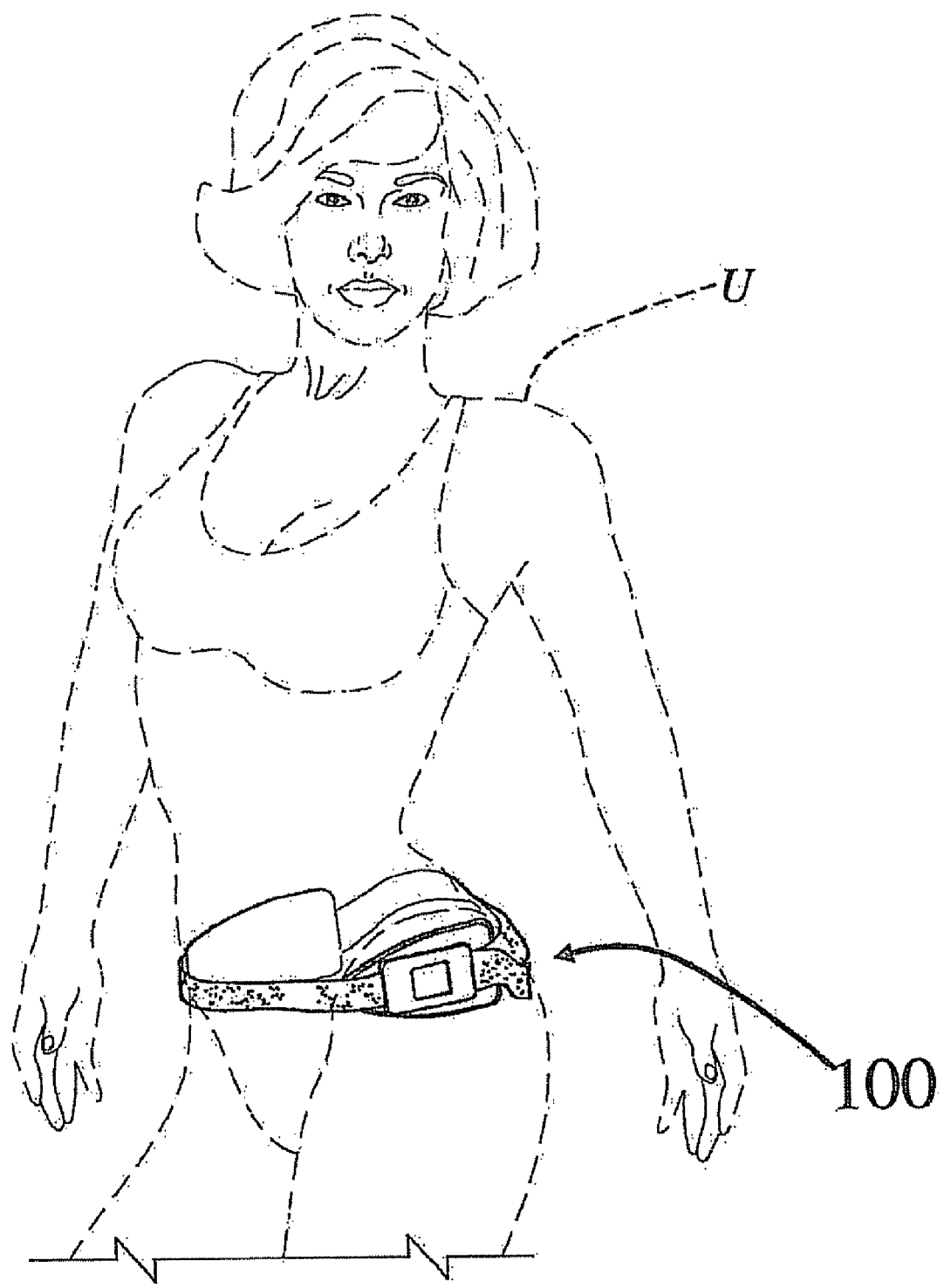
FIG. 1A is a perspective of the environmental view of an apparatus to treat menstrual cramping according to one embodiment of the present invention.

The present invention relates to a method and apparatus to non-chemically relieve menstrual cramping through use of compression at or proximate to the greater trochanters. Throughout the embodiments described below, an apparatus to treat menstrual cramping is denoted by the numeric label 100 as shown in FIG. 1A.

Figure 1B:
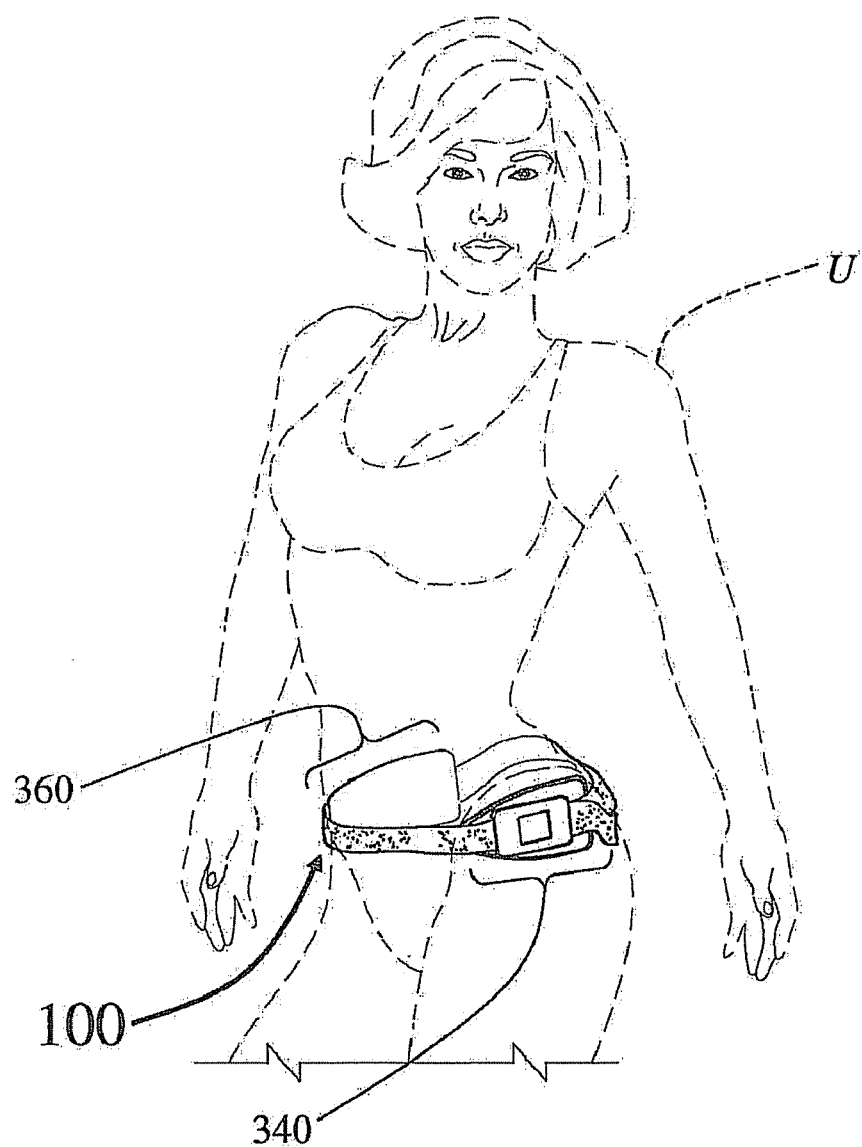
FIG. 1B is a further perspective environmental view of the apparatus to treat menstrual cramping of FIG. 1A.

The typical cause of menstrual cramping is excessive stretching of the muscles and tendons surrounding the uterus when expelling unwanted materials on the inner uterine wall during menstruation. When these muscles contract too fast or hard, it results in stretching of tissue resulting in the pain and discomfort associated with menstrual cramping. FIG. 1B illustrates how the apparatus 100 includes a left pad member 340 and a right pad member 360 laterally placed at each side of the user's (U) body near or proximate to the hips. By placing both pad members 340 and 360 proximate to the greater trochanters (located below the hips) and creating sufficient compression, the apparatus 100 decreases the stretching of tendons and ligaments surrounding the uterus, thus relaxing the tissue and alleviating cramping after a period of time and regiment of use.

A more detailed view of the individual components of one embodiment of apparatus 100 is offered by FIG. 2A. The apparatus 100 includes one or more essentially planar pads, preferably a left pad 180 and right pad 200. When assembled in the apparatus 100, each pad 180 and 200 provides a vertical surface for contact with the lateral sides of the user's (U) body proximate to the hips.

Each pad 180 and 200 is preferably made of two-part construction which includes a semi-rigid or hard outer side 680 and a more flexible and compressible inner side 620 (described in FIG. 6 below). In addition to at least one pad 200, the apparatus 100 also comprises one or more straps 120, each having an inner side 300 and an outer side 320. Each strap 120 likewise has a first end 280 and a corresponding second end 260 (shown in FIG. 6) connected to each other via a fastener 140.

In the embodiment shown in FIG. 2A, the fastener 140 is a push-button release type system located at or proximate to the left pad 180. However, such fastener 140 can be located anywhere along the circuit of the apparatus 100. Here, the push button fastener 140 has an exterior side 380, an interior side 400 (described in FIG. 8B below), a first end 420 and a second end 440. The fastener 140 is attached to the outer side 320 of the strap 120. While a push-button type system is one means for securing the first end 280 and corresponding second end 260 of the strap 120, any other acceptable fastening system may be used. This can include a latch system, a buckle system, Velcro, or any fastening system known to those skilled in the art.

FIG. 2B provides another perspective of the apparatus 100 illustrated in FIG. 2A, showing a more detailed assembly of the right pad member 360. In this embodiment, the strap 120 connects to the right pad member 360 through a sleeve 160 of sufficient shape and size as to receive the strap 120. The invention is not restricted to use of a sleeve 160 to connect each pad member 340 or 360 to the one of more straps 120 of the apparatus 100. Rather, one of ordinary skill in the art can use any known system to affix or connect each strap 120 to each pad member 340 or 360. However, it is preferable that such system allow at least one pad 180 or 200 to move along the circuit of the strap(s) 120 sufficient to place properly place both pads 180 and 200 proximate to the user's (U) hips.

Figure 3:
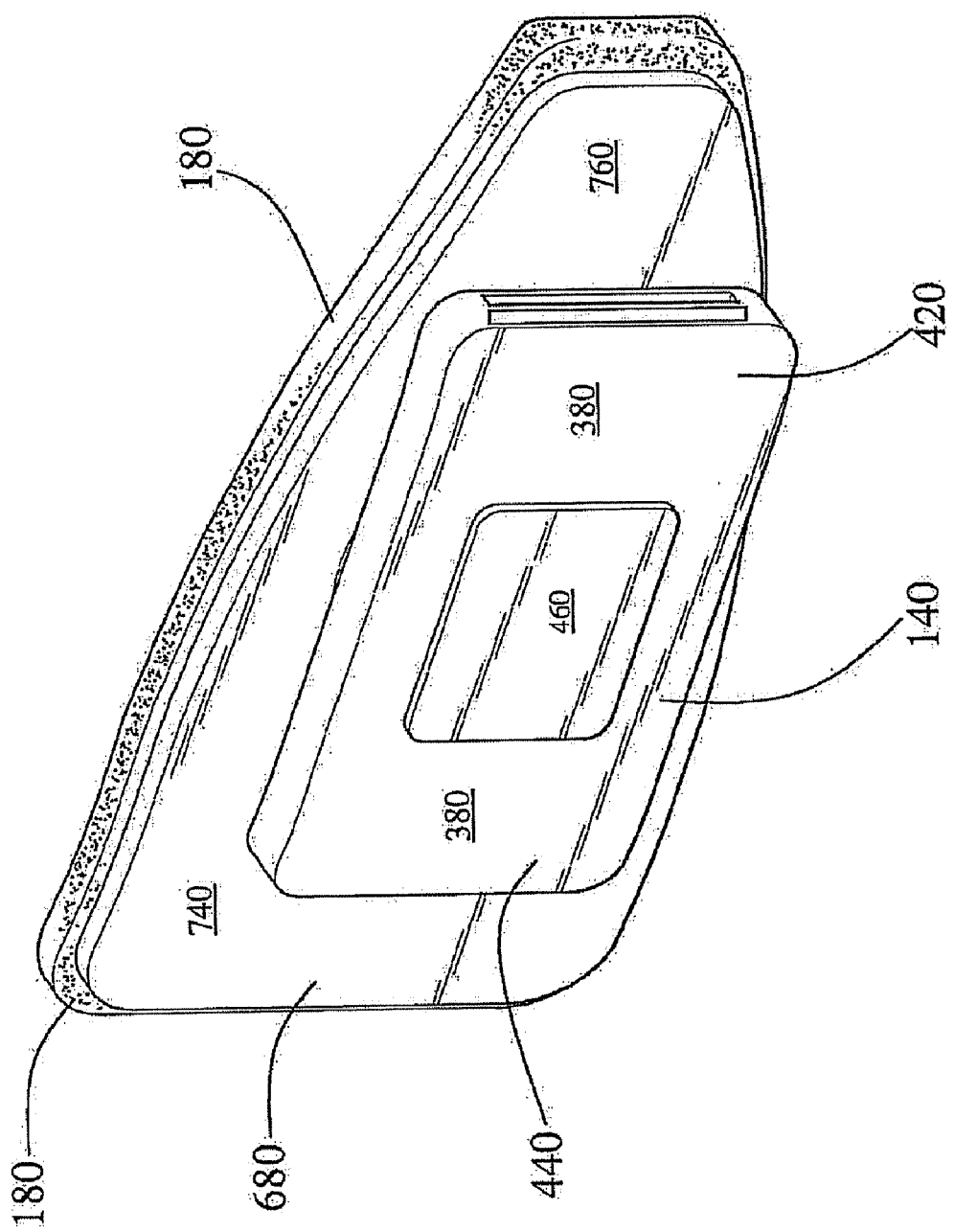
FIG. 3 shows a perspective view of the left part of an apparatus of FIG. 2A.

A more detailed perspective of the left pad 180 and fastener 140 is provided in FIG. 3. As illustrated, each pad has a front portion 760 and a rear portion 740. While the illustrated shape of each pad 180 (and 200) is tapered from the rear portion 740 to the front portion 760, a variety of shapes may be used based upon the user's (U) preference. One preferred shape is where both the rear portion 740 and front portion 760 are symmetrically tapered from the center of the pad 180 (as shown in more detail in FIG. 15 below). The invention also contemplates creating a mold of the user's (U) hips sufficient to create a custom shape for both the left pad 180 and right pad 200. The invention further contemplates making the outer side 680 of each pad 180 and 200 of a sufficiently malleable and formable material which can be formed to mirror the unique shape of the user's (U) hips.

Figure 4:
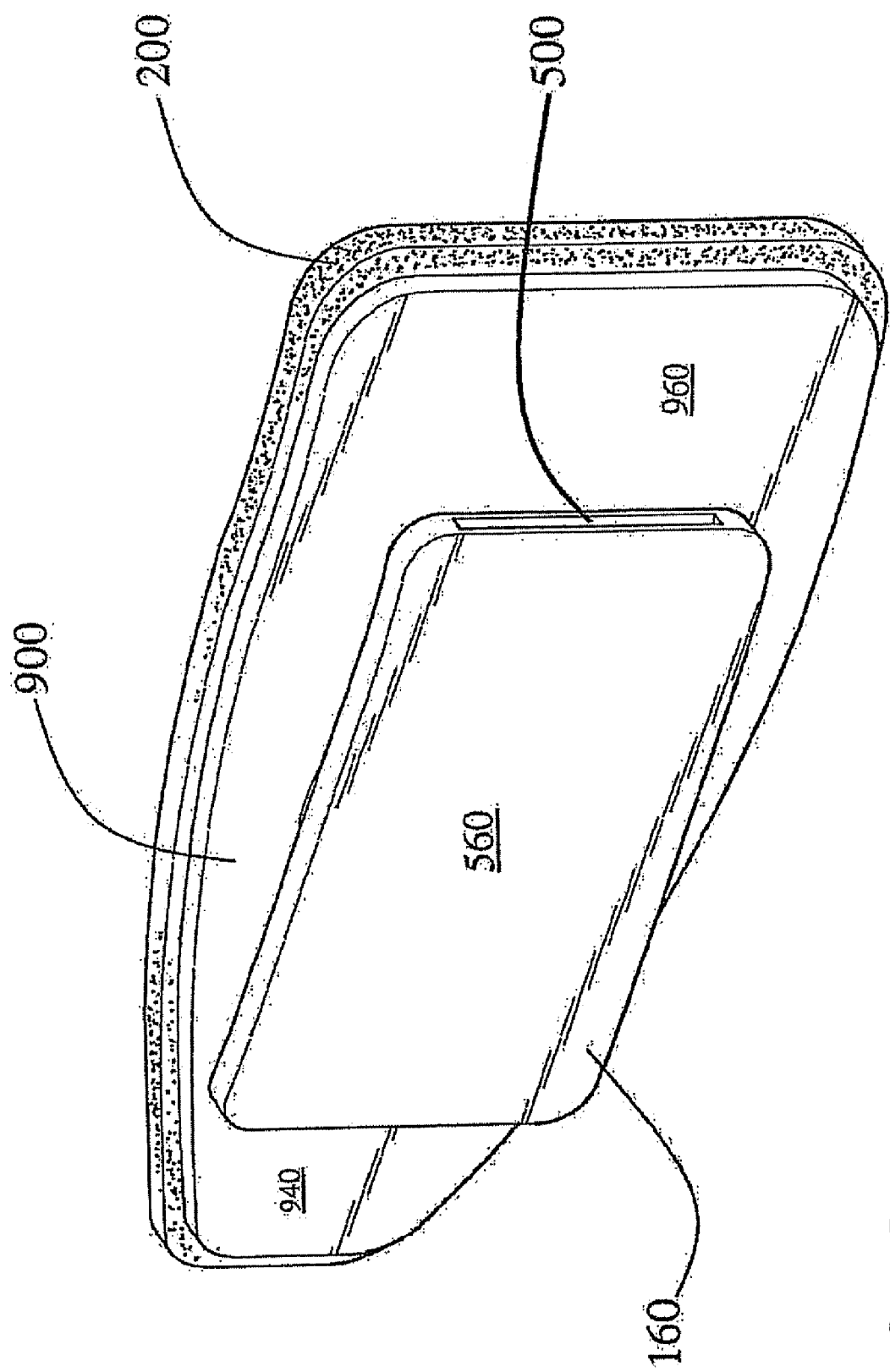
FIG. 4 shows a perspective view of the right part of the apparatus of FIG. 2B.

FIG. 4 provides a more detailed illustration of the right pad 200 and sleeve 160. Similar to the left pad 180, the right pad 200 has a front portion 940 and a rear portion 960. Likewise, the right pad 200 tapers from the rear portion 960 towards the front portion 940. Again, the sleeve 160 is shaped to have a bore-through hollow opening 500 of sufficient size and shape as to receive one or more straps 120. As discussed in more detail below in FIGS. 13(a) and 13(b), the present invention includes (in addition to the fastener 140) a constricting device 1100 to be located on or proximate to a pad 200. The constricting device 1100 can be a ratchet, pulley system or any similar mechanism which creates compression known to those ordinarily skilled in the art.

Figure 5:
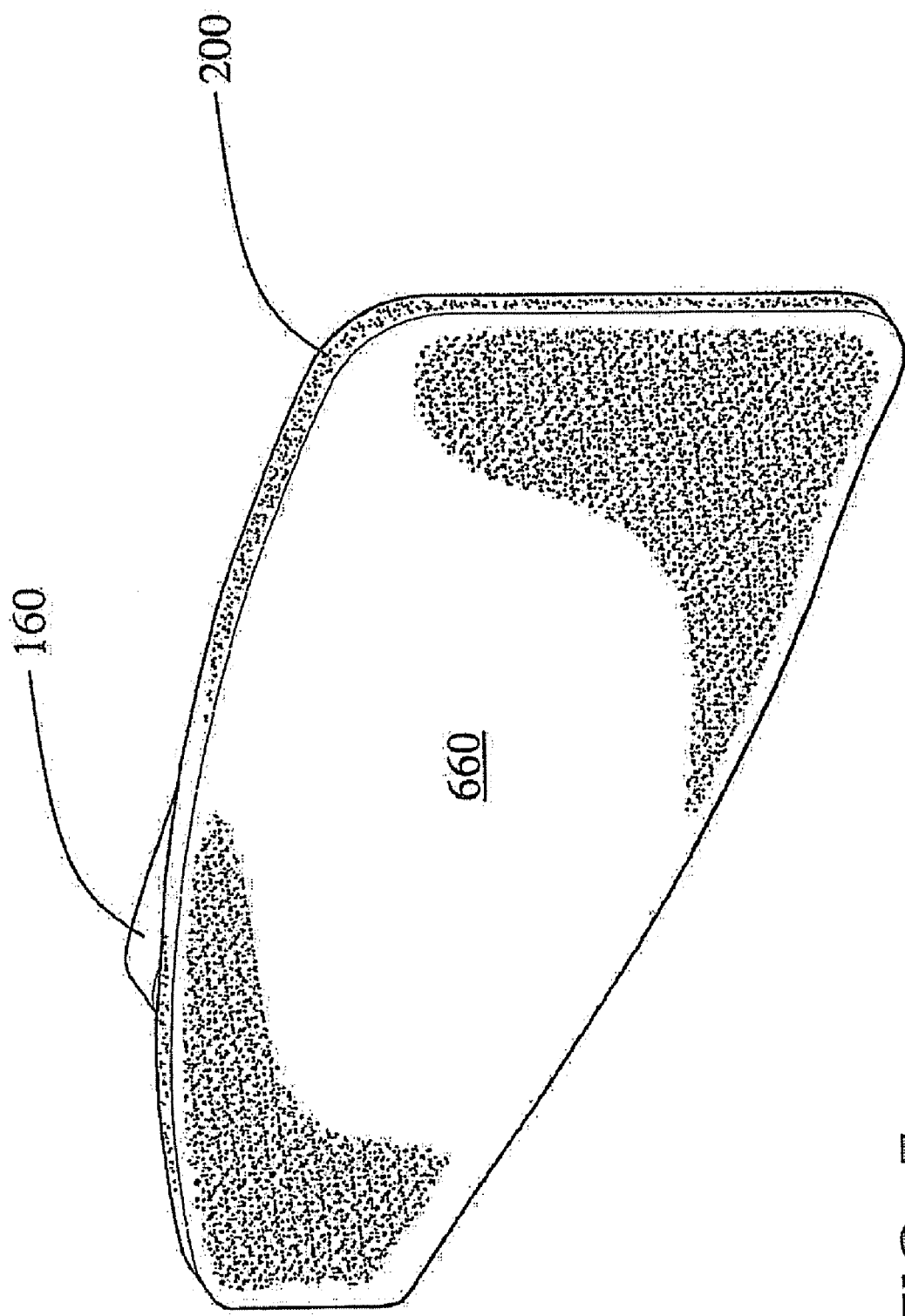
FIG. 5 shows a perspective view of a right pad of the apparatus.

A more detailed view of the inner side 660 of the right pad 200 is offered by FIG. 5. As the inner side 660 has direct contact with the user's (U) hips, it should be made of foam, neoprene or another compressible and hypoallergenic material known by those skilled in the art. It is also preferred that each pad 180 and 200 includes an outer housing 161 (shown in FIG. 14(b) and described below) to maintain the components of each pad, including the semi rigid outer side 680 and inner side 660. Such outer housing 161 should be washable and also hypoallergenic.

In addition to the malleable properties of each pad's two-part construction, one embodiment of the apparatus 100 includes use of vertical rotatable members to connect the strap(s) 120 to each pad 180 and 200, to greater conform to the individual shape of each user's (U) hips. FIG. 6 offers a partial cut away top view of both the left pad member 340 and right pad member 360, which includes these vertical rotatable members. The right pad member 360 illustrated in FIG. 6, includes a right pad 200 comprising a front portion 940 and a rear portion 960, which includes a semi-rigid outer side 900 and a flexible and compressible inner side 660. Located at the center of the semi-rigid outer side 900 of the right pad 200 is a female receiving notch 980 for use in connecting the sleeve 160 with a rotatable male swivel bracket 920 having an upper wall 1000. The female receiving notch 980 has a cavity 692, created by a flat upper wall 690 parallel with the semi-rigid outer side 900 of the right pad 200, sufficient to receive the rotatable male swivel bracket 920. The sleeve 160 is affixed to the upper wall 1000 of the rotatable male swivel bracket 920 to ultimately connect with the right pad 200 to form the right pad member 360. As illustrated, the sleeve 160 has a front portion 540 and a rear portion 520, and an outer side portion 560.

Figure 6:
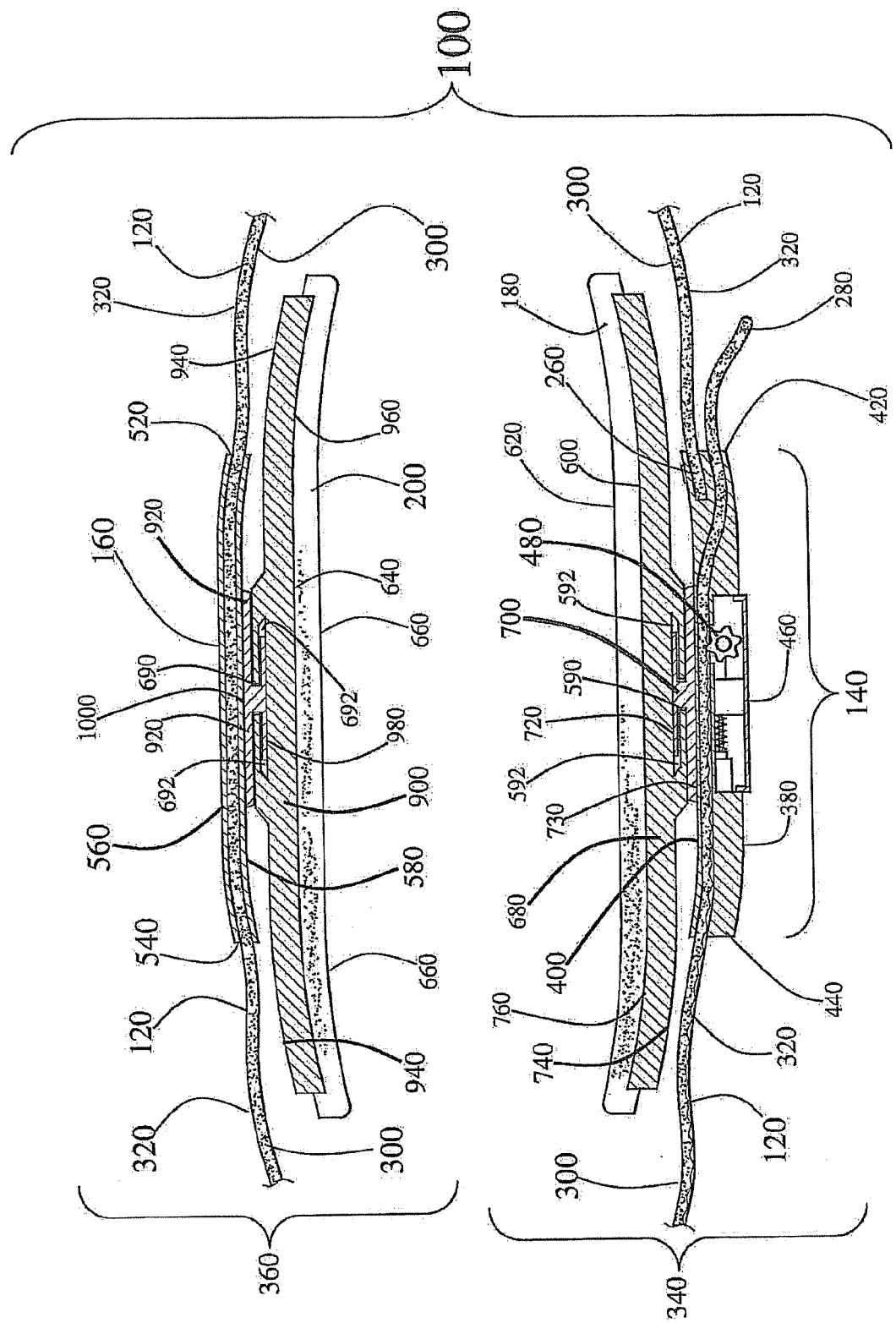
FIG. 6 shows a partially cut away top view of the apparatus.

FIG. 6 also provides a more detailed view of the components of the left pad member 340, which in this embodiment positions the fastener 140 on the left pad 180. Just as with the right pad 200, the left pad 180 includes a semi-rigid or hard outer side 680 and a more flexible and compressible inner side 620. Attached to the semi-rigid outer side 680 is a female receiving notch 592, capable of receiving a rotatable male swivel bracket 700 having an upper planar member 720 and a lower planar member 730 connected to interior side 400 of the fastener 140. The fastener 140 depicted in FIG. 6 has an exterior side 380, a first end 420, a second end 440, and a push button 460 to release the first end 280 of the strap 120. The second end 260 of the strap 120 is attached to the fastener 140 at or near its first end 420. Release of the first end 280 of the strap 120 is achieved through a spring-action member 480.

FIG. 7 illustrates how the embodiment show in FIG. 6 allows the left pad 180 to rotate into a position which conforms with the user's (U) unique hip shape.

Figure 8A:
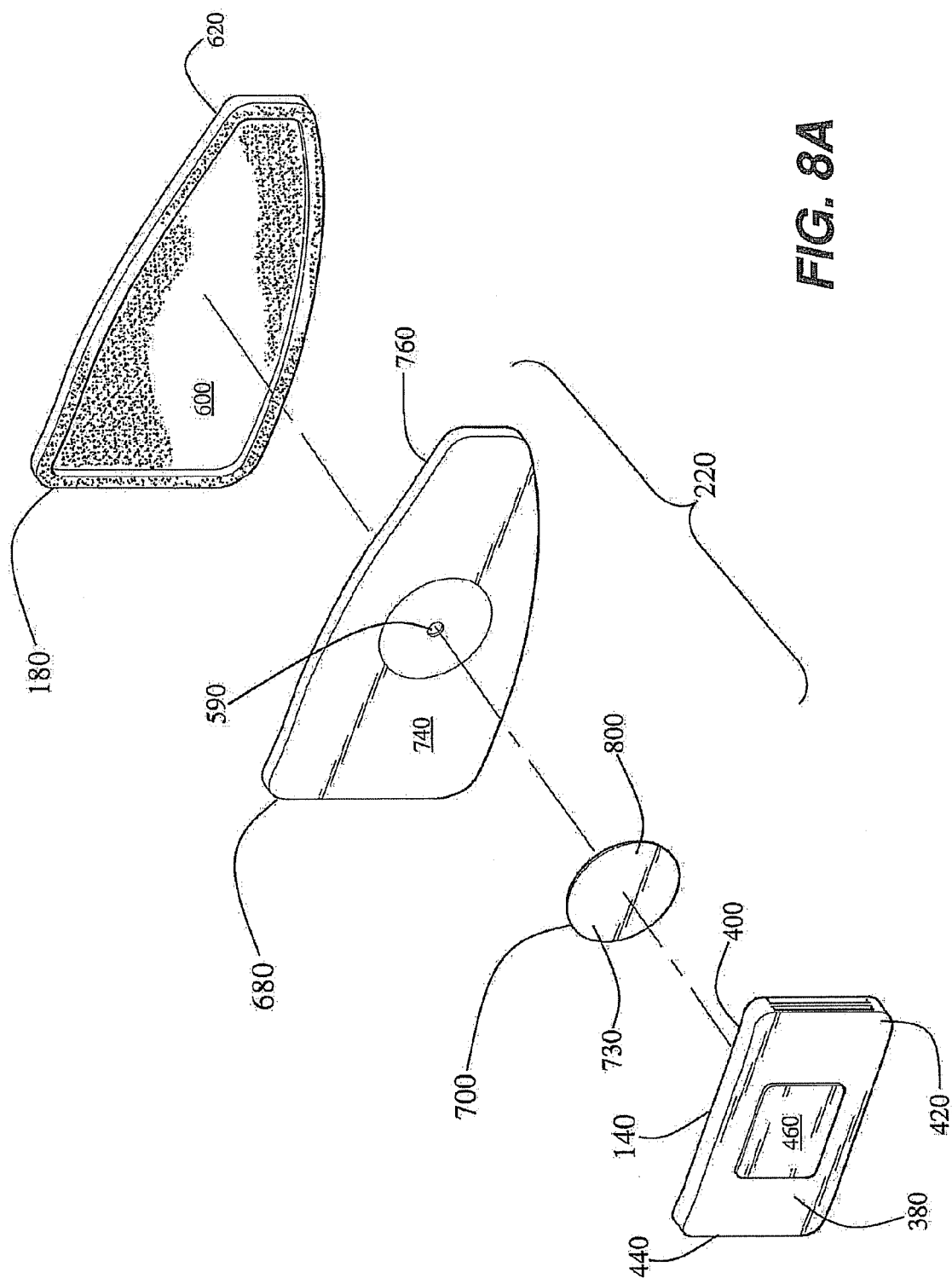
FIG. 8A shows an exploded view of the left pad of the apparatus.
Figure 8B:
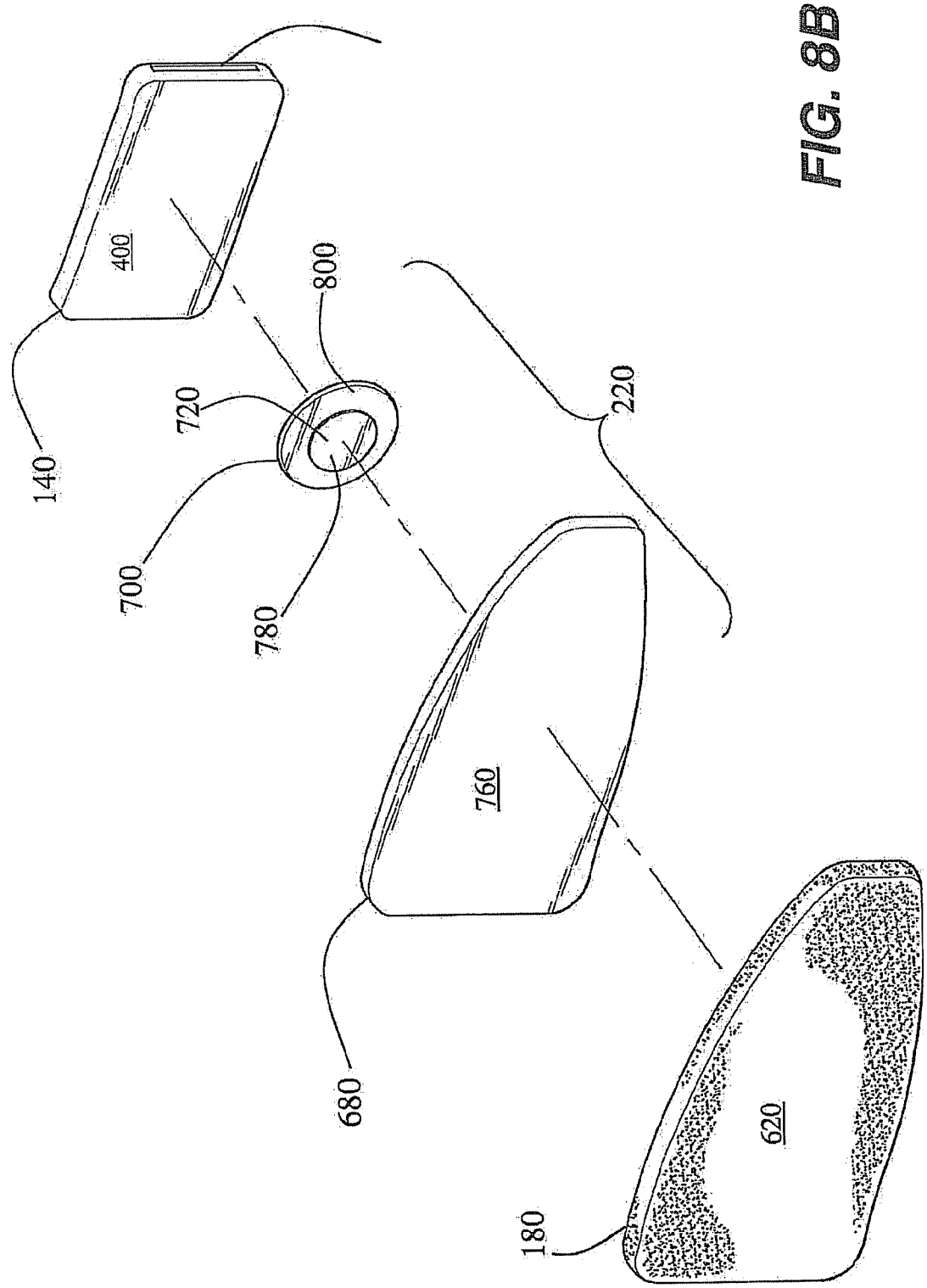
FIG. 8B shows a further exploded view of the left pad of the apparatus.

FIG. 8A is an exploded view of the left pad 180 shown in FIGS. 6 and 7. As shown, the fastener 140 having a push button release 460 is connected to the left pad 180 at its interior side 400 to the lower planar member 730 of the swivel bracket 700. Here, the bracket is a circular disc 800, which attaches to a corresponding circular recess 590 located on the semi-rigid outer side 680 of the left pad 180. The semi-rigid outer side 680 then connects to the flexible and compressible inner side 620 at its outer portion 600. Combination of the swivel bracket 700 and both the inner 620 and outer 680 sides of the left pad 180 comprise the left swivel member 220 of the apparatus 100. FIG. 8B represents a 180 degree view of the left pad 180 shown in the exploded view of FIG. 8A.

Figure 9:
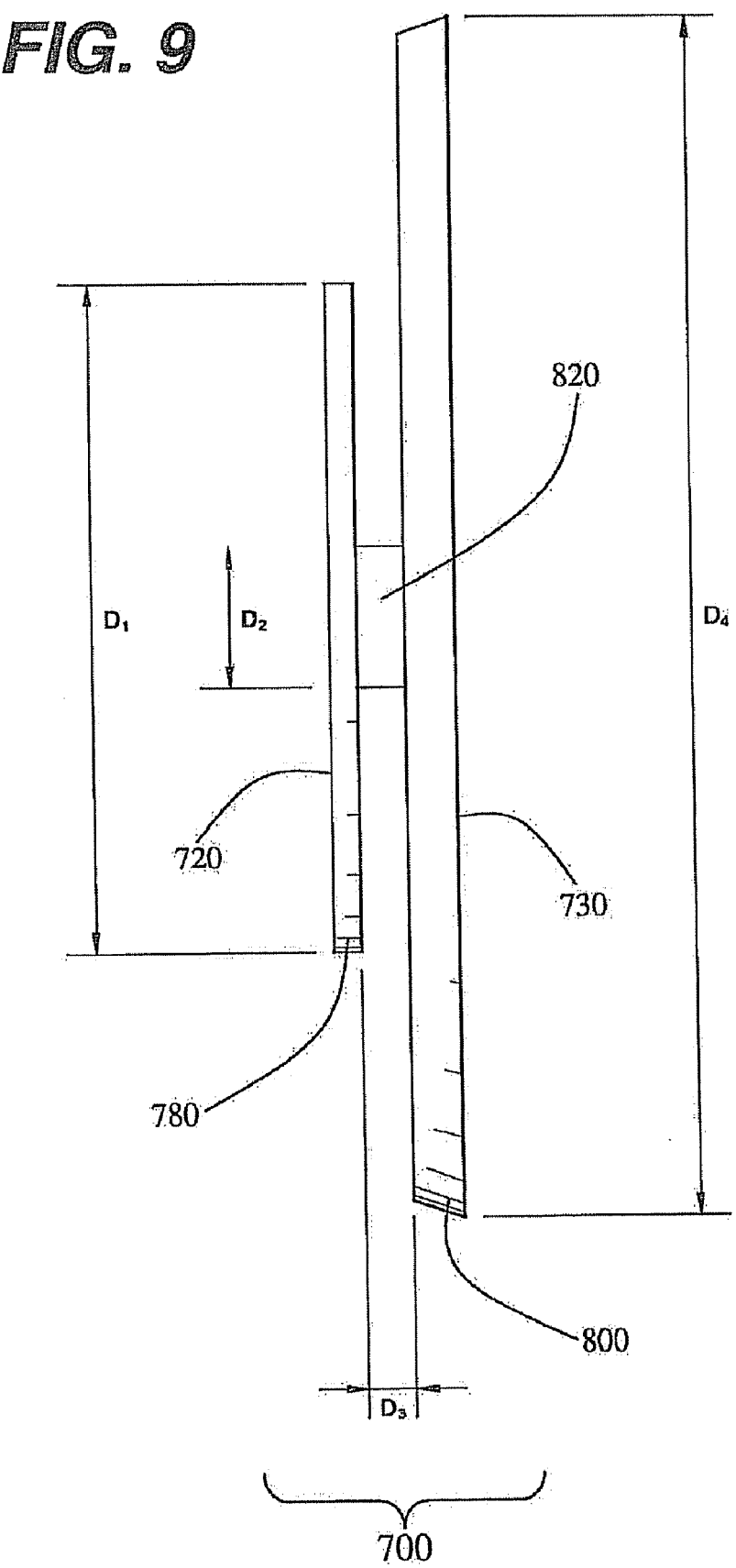
FIG. 9 shows a side view of the secondary left swivel-bracket.
Figure 9B:
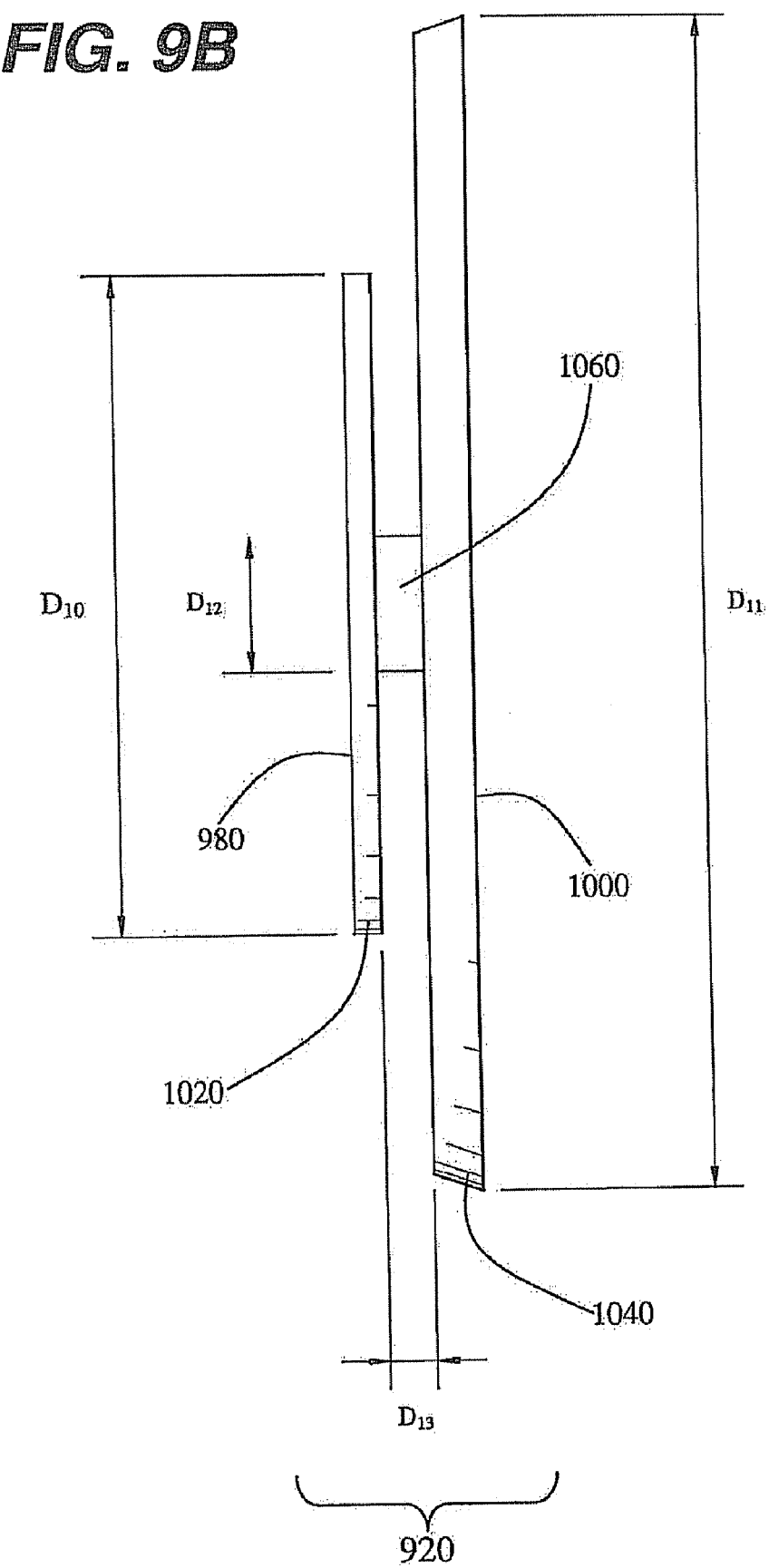
FIG. 9B shows a side view of the secondary right swivel-bracket.

Detailed description of FIGS. 9 and 9B are incorporated by reference from the parent application.

FIG. 10A is an exploded view of the right pad 200 of FIG. 6. Here, the sleeve 160 connects with the circular bracket 920 at the sleeve's 160 back portion 580. The circular bracket 920 is of two-part construction having a larger circular outer ring 1040 and a smaller circular inner ring 1020. The smaller circular inner ring 1020 connects with exterior side 900 of the right pad 200 at its upper side 980. FIG. 10B represents a 180 degree view of the right pad 200 shown in the exploded view of FIG. 10A.

Figure 11:
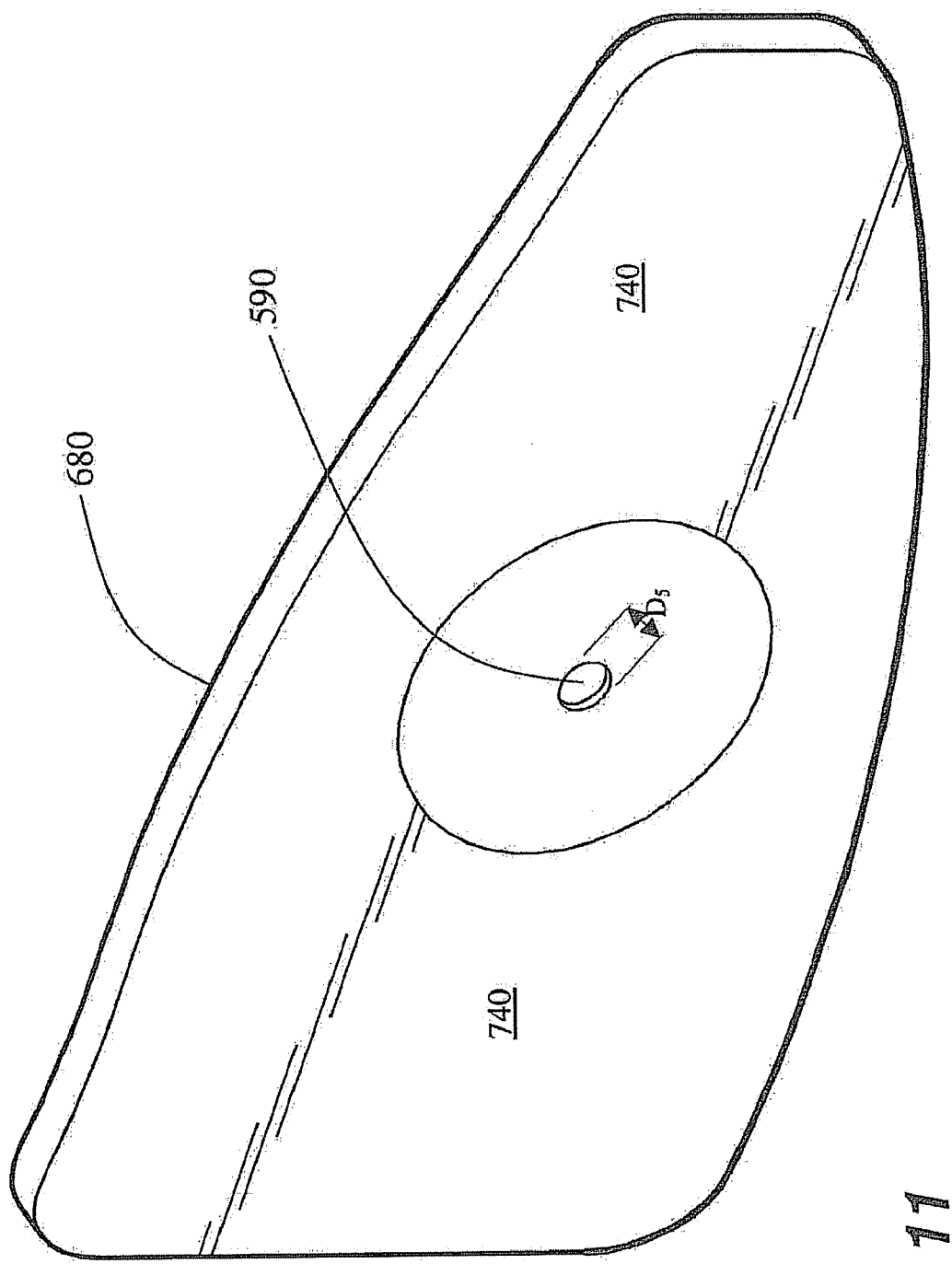
FIG. 11 shows a view of the primary left swivel bracket.
Figure 12:
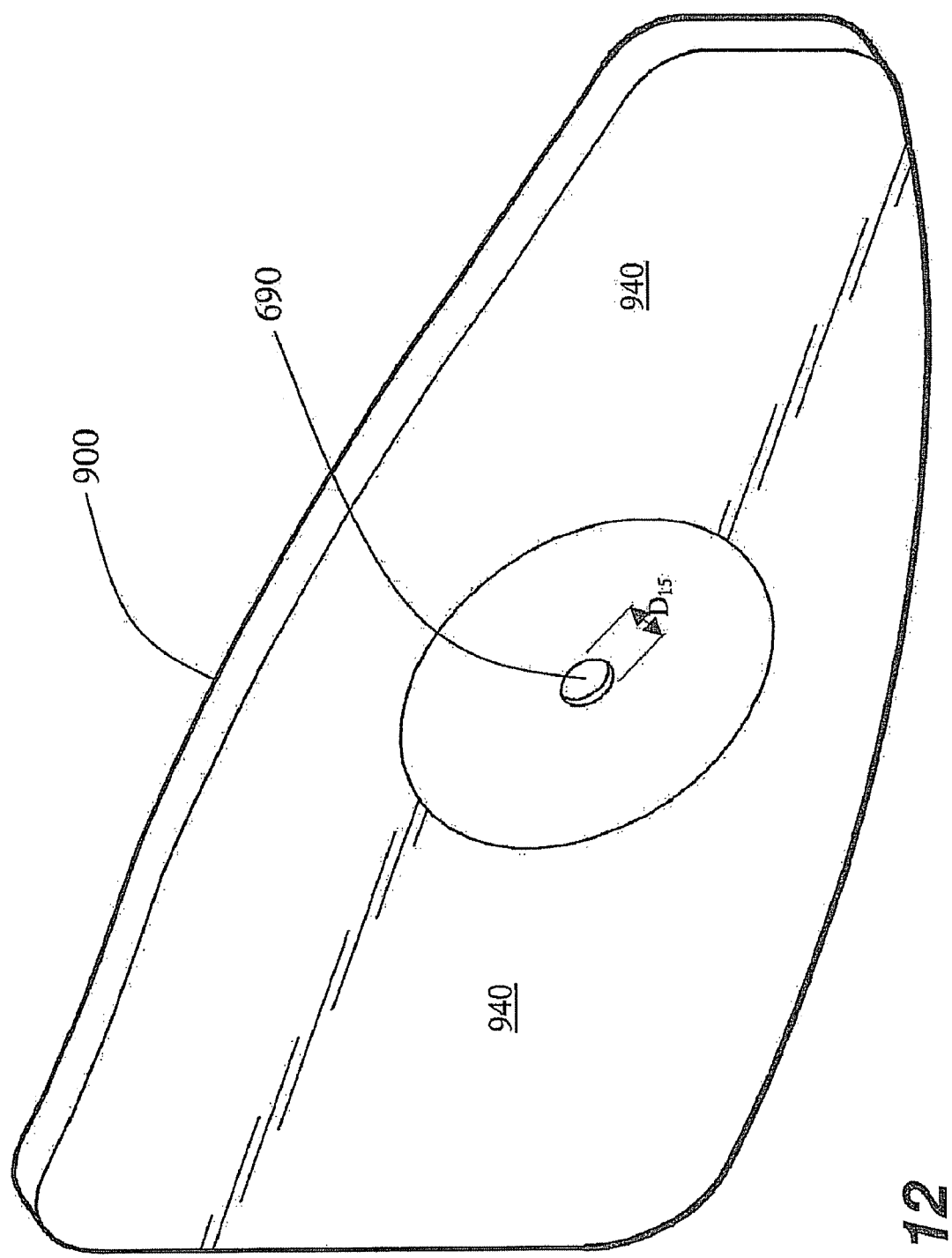
FIG. 12 shows a view of the primary right swivel bracket.

FIGS. 11 and 12 both offer perspective views how the semi-rigid outer members 680 and 900 of the left pad 180 and right pad 200 connect with the smaller circular inner rings 1020 of each swivel bracket 920. FIG. 11 illustrates how the left pad 180 includes a recess 590 of sufficient size and dimension to receive the smaller circular ring 1020 of the swivel bracket 920. Likewise, FIG. 12 shows a similar recess on the flat upper wall 690 of the semi-rigid outer side 900 of the right pad 200 sufficient to receive the rotatable male swivel bracket 920.

Figure 13A:
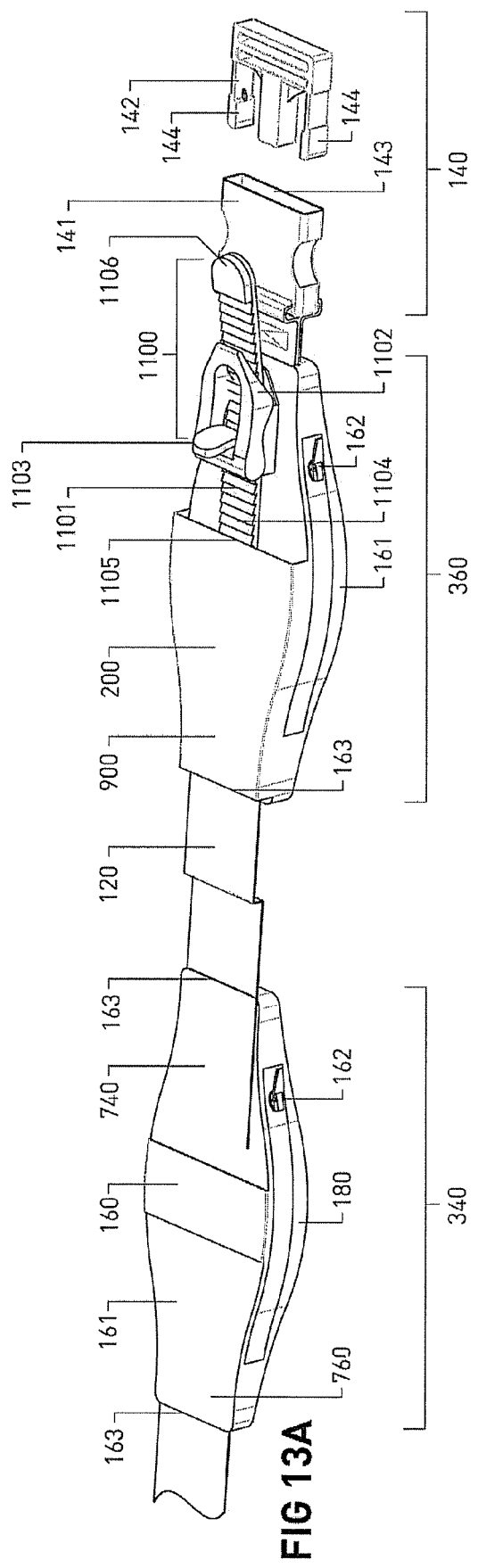
FIGS. 13(a) and 13(b) show a perspective view of two embodiments of a constricting device.
Figure 13B:
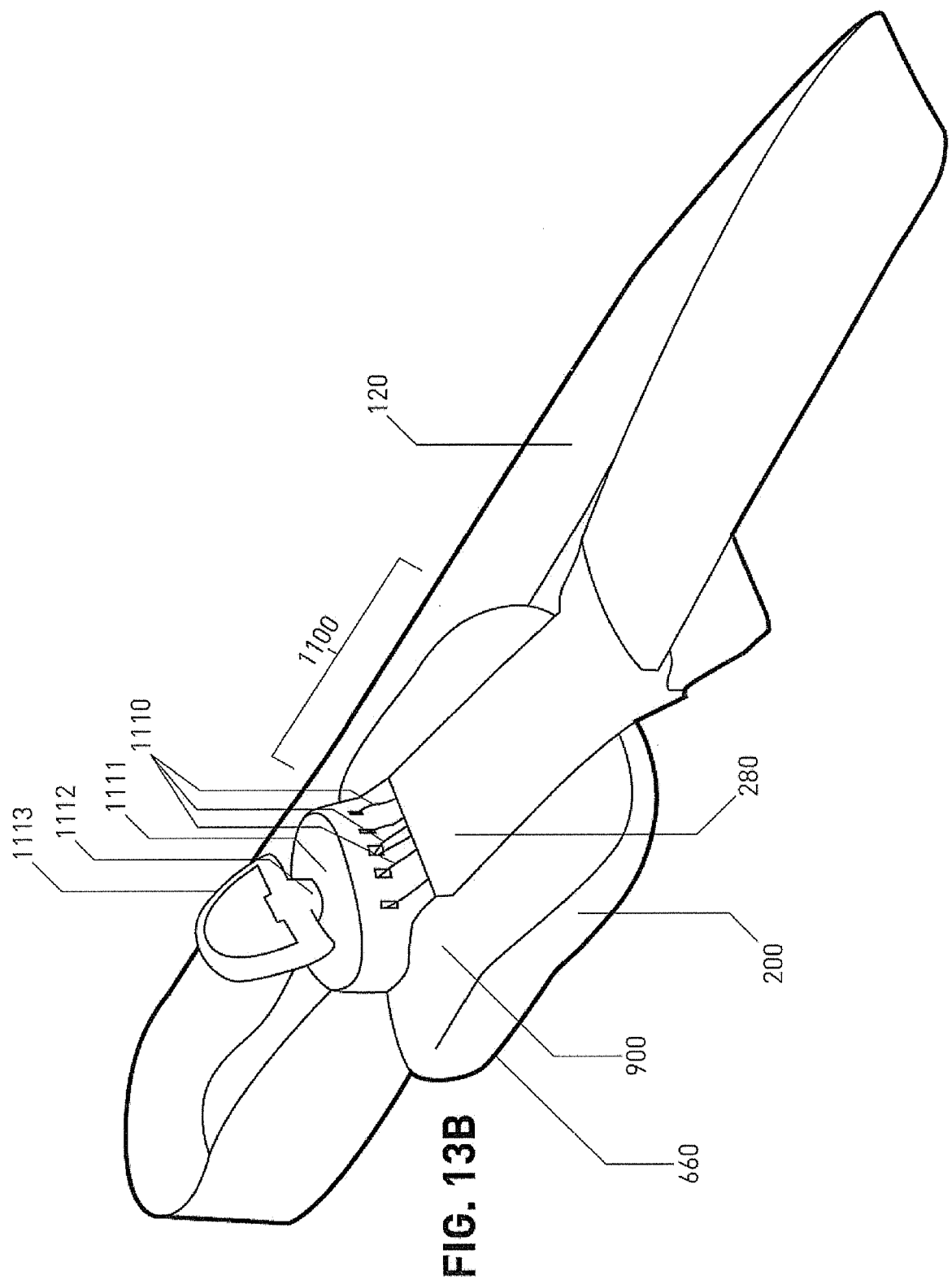

FIGS. 13(a) and 13(b) are perspective views of two different embodiments of the constricting device 1100 affixed to the right pad 200. FIG. 13(a) shows the fastener 140, as a buckle system, having a first fastener 141 and a corresponding second fastener 142. The first fastener 141 has an opening 143 of sufficient size and dimension to receive the one or more flexible prongs 144 of the corresponding second fastener 142.

The constricting device 1100 illustrated in FIG. 13(a) is a ratchet, having a ratchet strap 1101 with multiple teeth 1104, which is fed into a locking member 1102. The locking member 1102 is connected the semi-rigid outer side 900 of the right pad 200. The ratchet strap 1101 has a back portion 1105 and front portion 1106. The back portion 1105 is connected to the first end 280 of the strap(s) 120. The locking member 1102 includes a rotatable handle 1103, which rotates back and forth sufficient to pull the teeth 1104 of the ratchet strap 1101 to tighten, as well as release to reduce and/or eliminate compression. Both the right pad 200 and left pad 180 of the embodiment are encased by an outer housing 161 secured by a zipper system 162.

Another embodiment of the constricting device 1100 is the pulley system shown in FIG. 13(b). This pulley system is connected to the semi-rigid outer side 900 of the right pad 200. Here, the constricting device 1100 is comprised of multiple strings 1110 connected to the first end 280 of the strap(s) 120. Each of the strings 1110 pass through a rigid pulley chamber 1111, and connect to a circular spindle 1112. Affixed to the top of the spindle 1112 is a rotatable exterior handle 1113. Through the mechanical advantage of twisting the strings 1110 around the spindle 1112, the strings 1110 are pulled into the rigid pulley chamber 1111, which in turn constricts the strap(s) 120.

Figure 14A:
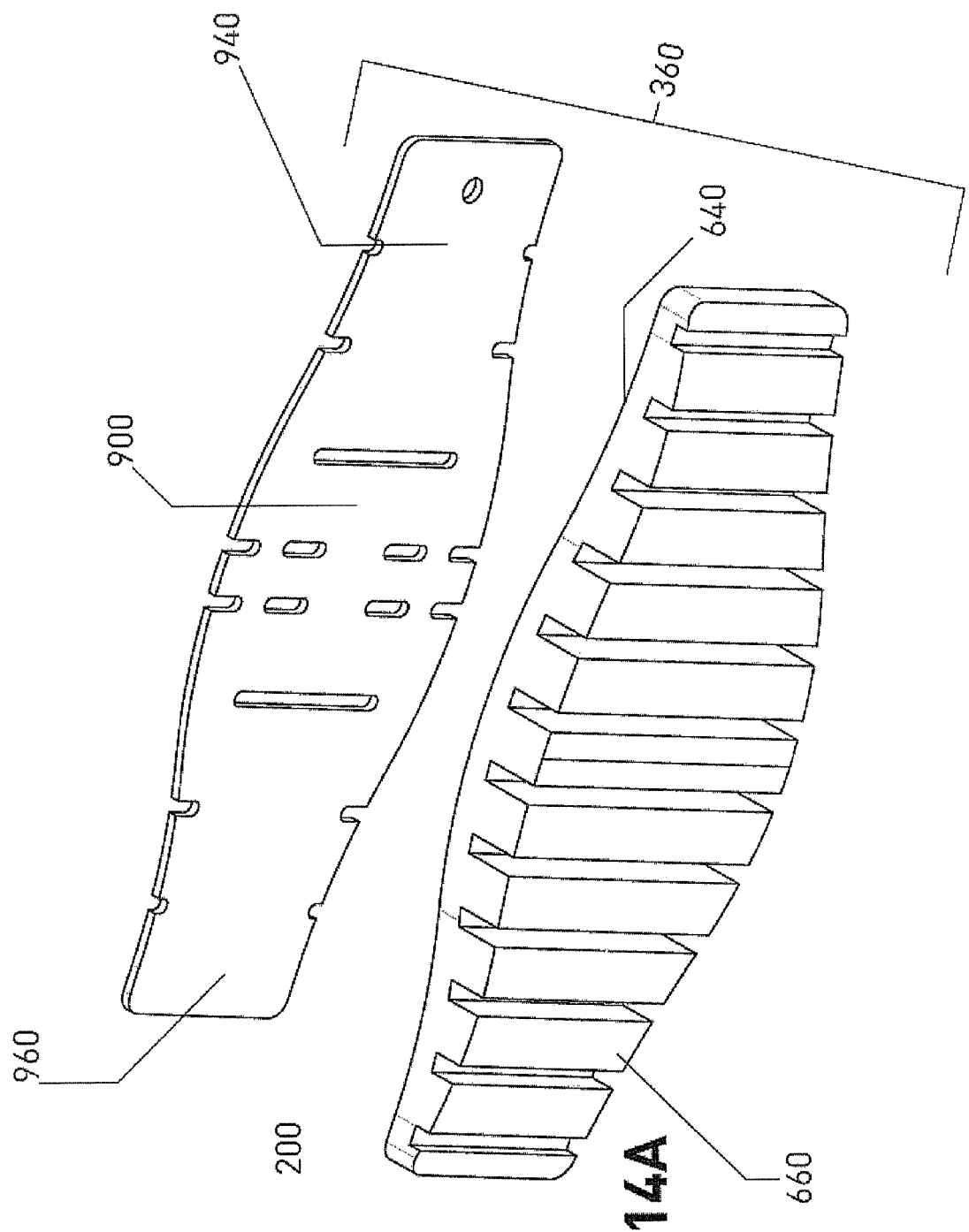
FIGS. 14(a) and 14(b) show two different embodiments of the two-part construction for each pad.
Figure 14B:
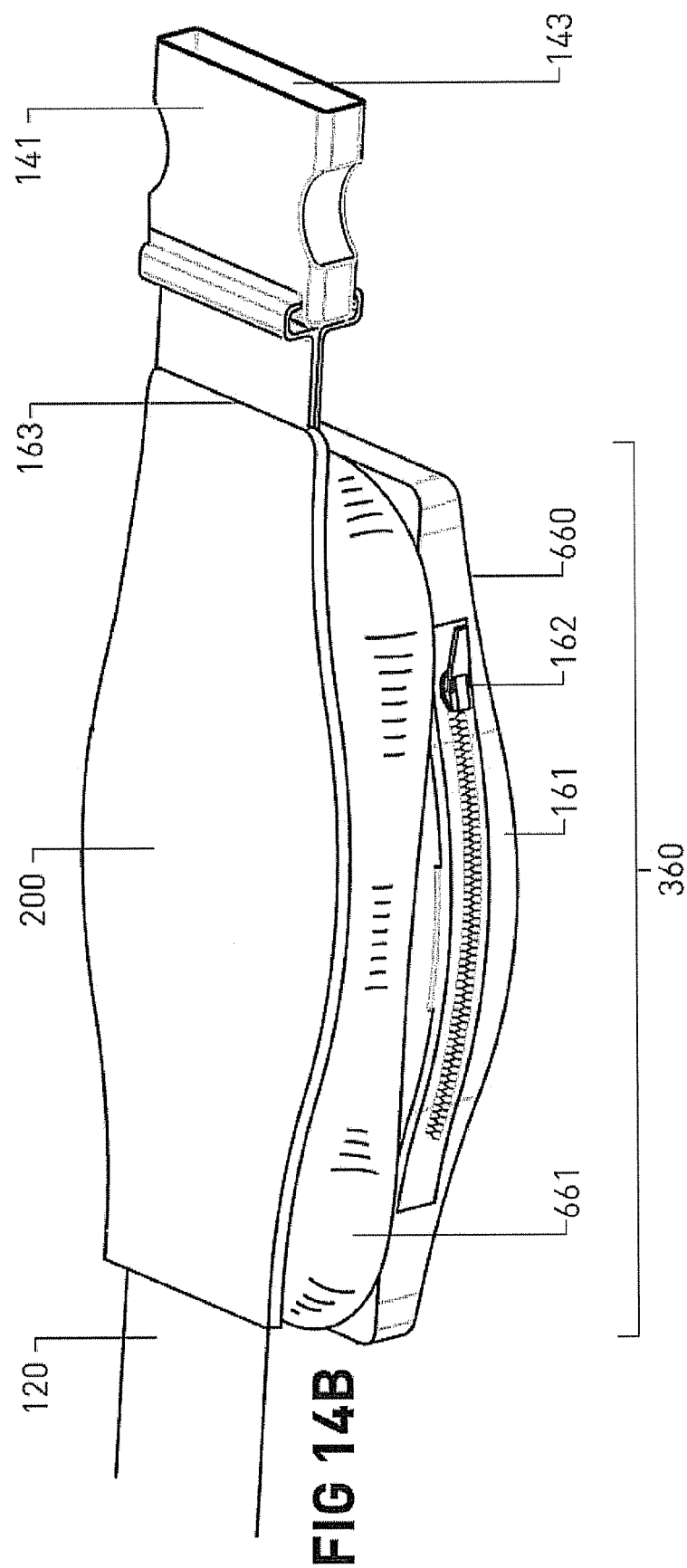

FIGS. 14(a) and 14(b) illustrate two different embodiments of the two-part construction of the pad 200. FIG. 14(a) is an exploded view showing how the pad member 360 includes a semi-rigid outer side 900 and a flexible compressible inner side 660. The semi-rigid outer side 900 has a front portion 940 and rear portion 960 and rests on the back 640 of the compressible inner side 660. The semi-rigid outer side 900 can be affixed to the strap(s) 120. The flexible compressible inner side 660 has a uniform stepped shape, such that when the apparatus 100 is compressed, the pad 200 can flex inward.

FIG. 14(b) shows another two-part construction for the right pad member 360. Here, the flexible compressible inner side 660 of the pad 200 is a liquid or gas filed inner bladder 661. The amount of liquid or gas which is placed in the inner bladder 661 can be adjusted to the user's (U) individual preferences. The inner bladder 661 is positioned or affixed on the semi-rigid outer side 900 of the pad 200. An outer housing 161 of sufficient size and dimension can be placed around both the bladder 661 and semi-rigid outer side 900, which can be closed via a zipper system 162. The housing 161 also contains a left and right opening 163 of sufficient size and dimension to allow the strap 120 to pass through and/or be affixed to the semi-rigid outer side 900.

Figure 15:
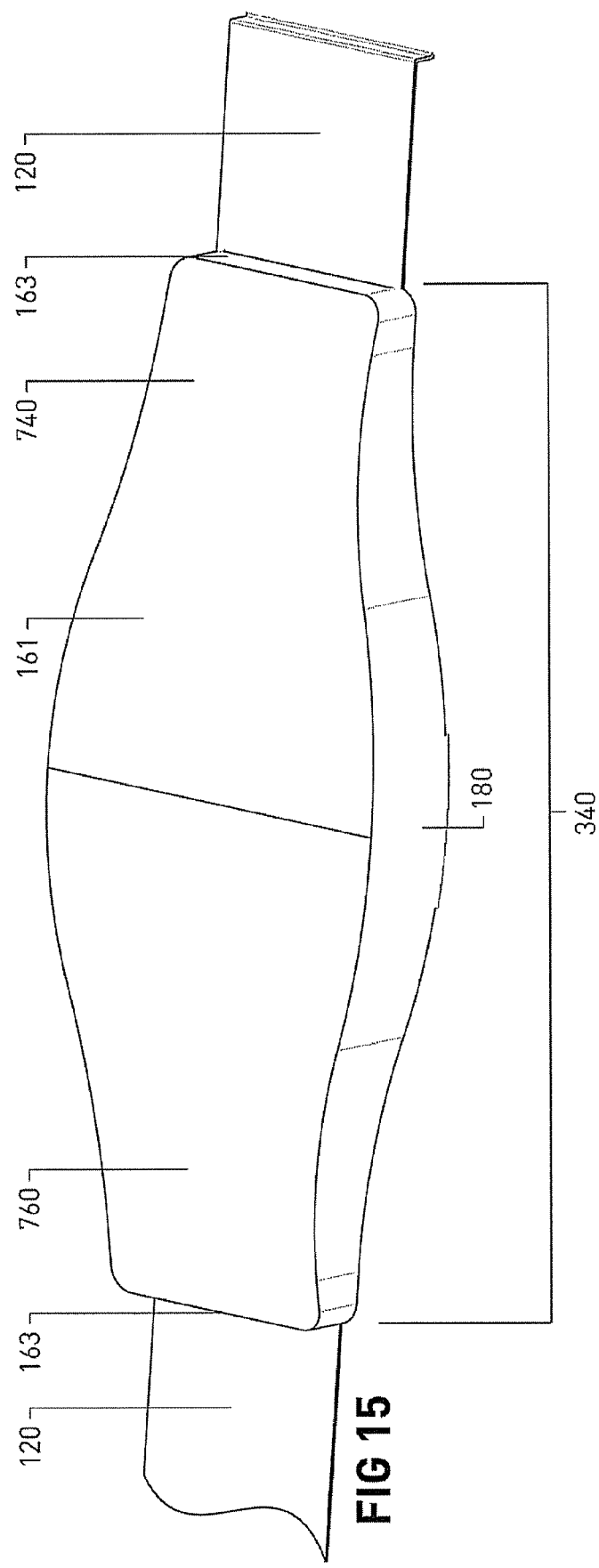
FIG. 15 shows a perspective view of the front of a pad having symmetrically tapered portions.

FIG. 15 shows a perspective of the left pad 180, where both the rear portion 740 and front portion 760 are symmetrically tapered from the center.

Figure 16:
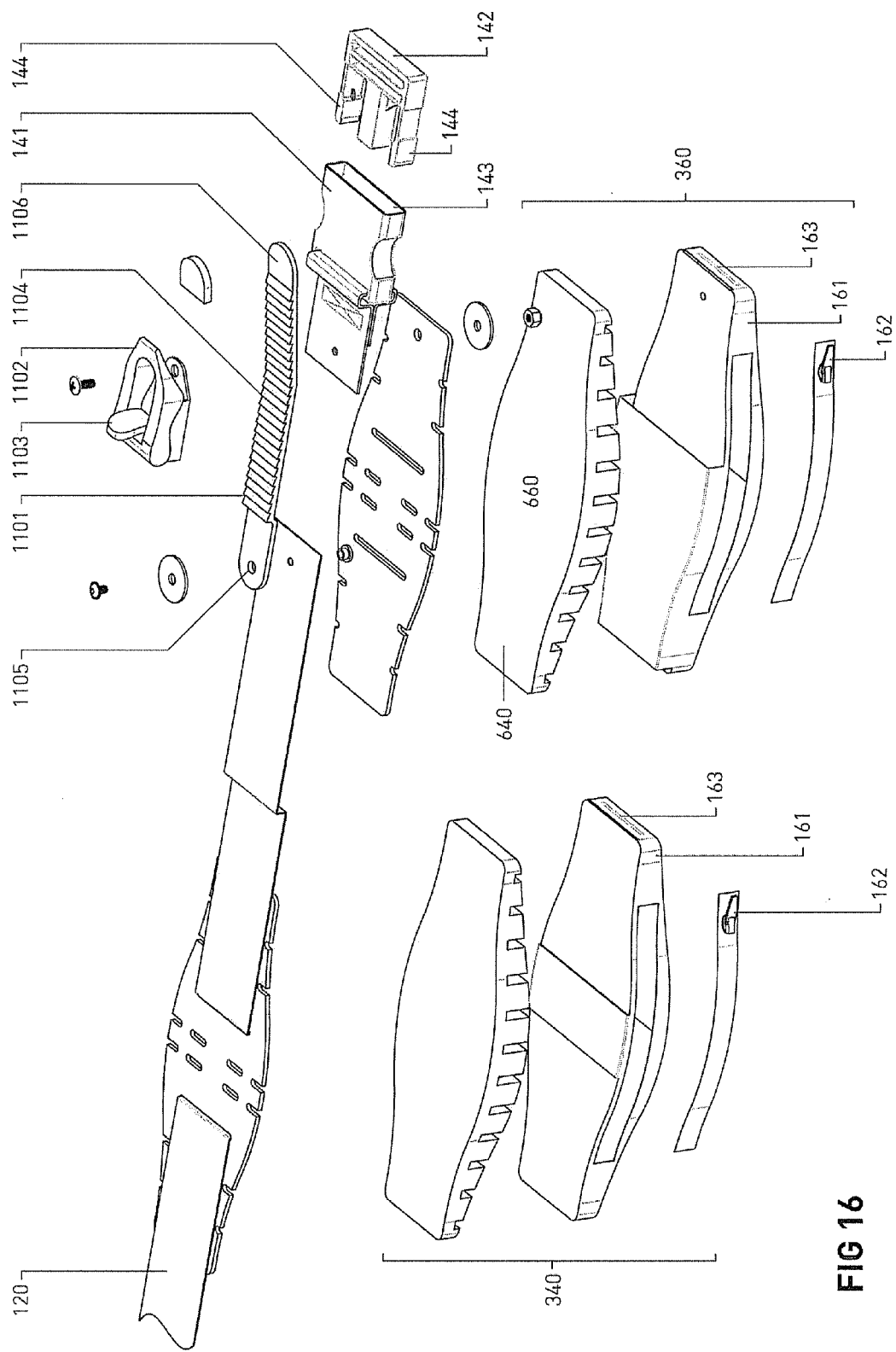
FIG. 16 shows an exploded view of one embodiment, which includes a ratchet as the constricting device.

FIG. 16 offers an exploded view of the components of the apparatus 100, where the constricting device 1110 is a ratchet. The embodiment illustrates how both the left pad 180 and right pad 200 are each placed into an outer housing 161. Each housing 161 has opening on both the right and left sides of sufficient size and dimension to allow the strap 120 to pass through. In this embodiment, the strap 120 is affixed to the left pad 180 and right pad 200. Each sleeve 160 is placed around the flexible compressible inner side 660, the semi-rigid outer side 900, as well as the strap 120, and secured by closing the zipper system 161. Here, the right pad member 360 is attached to the locking member 1102. The back portion 1105 of the ratchet strap 1101 connects with the first end 280 of the strap(s) 120. When the rotatable handle 1103 pivots back and forth, it engages the teeth 1104 of the ratchet strap 1101, which causes the apparatus 100 to compress.

Figure 17:
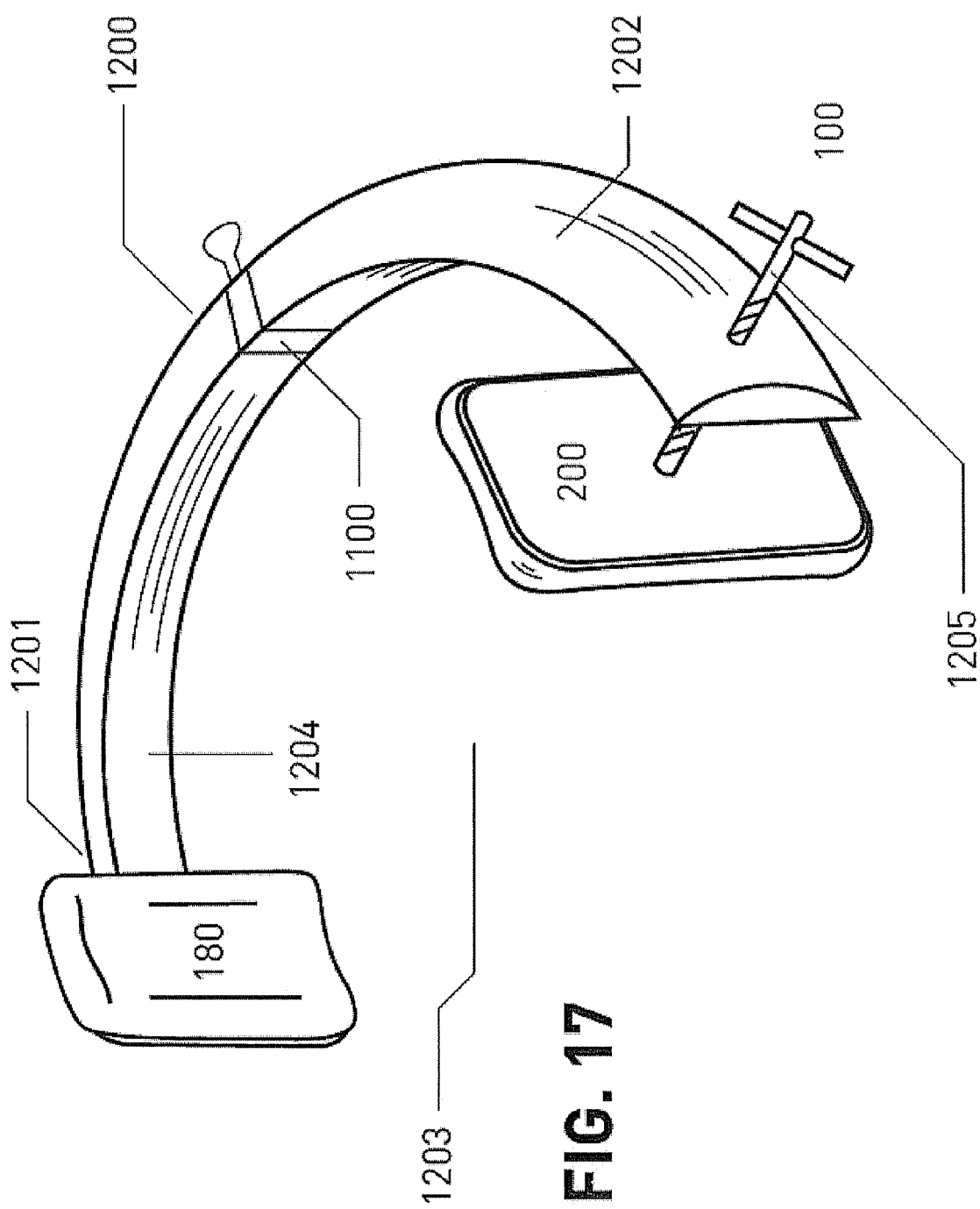
FIG. 17 shows a perspective view of another embodiment of the apparatus having a rigid C-shaped belt.

FIG. 17 shows an alternative embodiment of the invention where the strap 120 and fastener 140 described above is replaced by a rigid C-Shaped belt 1200. The belt 1200 has a first end 1201 and a corresponding second end 1202, with an opening 1203 of sufficient size and dimension to allow the belt 1200 to be placed around the user (U)'s hips. The apparatus 100 can include (but does not necessarily require) a compression device 1100, such as a spring, at or proximate to the center of the belt 1200 to create an internal compression force. At the inner side 1204 of the belt 1200, a left pad 180 and right pad 200 are attached. Here, the compression device 1100 can also be a screw based system 1205 to twist both pads 180 and 200 in place and to create a sufficient compression force onto the user's hips proximate to each greater trochanter. Under such a system, each pad 180 and 200 can be vertically rotated via the screw based system 1205 to conform to the individual user's hips and preference. Other systems, known to those ordinary skilled in the art, can be used to attach the pads 180 and 200 to the belt 1200 and to be compressed onto the user's (U) hips.

In addition to the apparatus 100, the invention also relates to a specific method of relieving the pain and discomfort associated with menstrual cramping. As previously discussed, the method is designed to reduce the stretching of ligaments and tendons surrounding the uterus during menstruation.

The general method of treatment requires use of an apparatus 100 as described above, or any similar mechanism which allows performance of the steps of: first, dimensioning one or more pads 180 and/or 200 proximate to the greater trochanters of the female user (U) and forming each pad to conform to their hips; second, affixing the pad 180 or pads 180/200 to one or more straps 120 having a first end 280 and a corresponding second end 260 at the opposite portion of the strap(s) 120; third, connecting the first end 280 and second end 260 of each strap 120; and fourth, creating a compression sufficient to compress each pad 180 or pads 180/200 onto said user (U). Between 10 to 15 pounds of pressure should be administered during each treatment, which each session lasting between 5 to 10 minutes after the user (U) reports the menstrual pain or discomfort has subsided. However, individual treatment regiments may vary as to both length and pressure.

Apart from the general method described above, the method of treatment may also include the step of filling an inner bladder 661 with sufficient liquid or gas as to conform with the unique shape of the user's (U) hips, if an internal bladder 661 as described in FIG. 14(b) is used. If desired, such bladder 661 could be heated to help further treat and alleviate the pain associated with menstrual cramping.

The method could further include the step of shaping each malleable pad 180 or pads 180/200 to conform with the shape of the user's hips. Moreover, the method could additionally include the step of rotating each pad to a position which further conforms with the shape of the user's (U) hips through use of the rotating member described in FIG. 6 and FIG. 7 above.

I claim:

1. An apparatus to relieve menstrual cramping, the apparatus comprising:
    one or more pads, wherein each pad has an outer side and an inner side;
    one or more straps, wherein each strap has a first end and a second end at the opposite portion thereof, as well as an outer side and an inner side, wherein at least one strap is affixed at its inner side to the outer side of the one or more pads;
    a fastener having a first fastener portion attached to the first end and a corresponding second fastener portion attached to the second end of each of the one or more straps; and
    a constricting device operable with the one or more straps and the one or more pads to create a compression force onto each of the one or more pads when the fastener portions are connected to each other, wherein the compression force is sufficient for decreasing a stretching of tendons and ligaments surrounding a uterus, thus relaxing tissue and alleviating menstrual cramping when the apparatus is secured to a torso of a user.

2. An apparatus to relieve menstrual cramping according to claim 1, wherein each of the one or more pads has a left tapered portion and a right tapered portion.

3. An apparatus to relieve menstrual cramping according to claim 2, wherein the left tapered portion and the right tapered portion are symmetrical to one another.

4. An apparatus to relieve menstrual cramping according to claim 1, wherein each outer side of the one or more pads is semi-rigid and each inner side is flexible and compressible.

5. An apparatus to relieve menstrual cramping according to claim 1, wherein at least one of the one or more pads contains an inner bladder filled with at least one of a gas or and liquid.

6. An apparatus to relieve menstrual cramping according to claim 1, where two pads are affixed at their outer sides to an inner side of each strap and dimensioned to be positioned laterally across a middle portion of a body of a user to make contact at or near hips of the user.

7. An apparatus to relieve menstrual cramping according to claim 1, where each of the one or more pads is made of a material sufficient to deliver heat to an area proximate greater trochanters of a user.

8. An apparatus to relieve menstrual cramping according to claim 1, wherein the constricting device is comprises a ratchet.

9. An apparatus to relieve menstrual cramping according to claim 1, wherein the outer side of each of the one or more pads is affixed to the inner side of each of the one or more straps through a swivel bracket.

10. An apparatus to relieve menstrual cramping, the apparatus comprising:
    one or more pads, each pad having an outer side and an inner side;
    a C-shaped belt having an inner side and an outer side; the outer side of each of the one or more pads connected to the inner side of the C-shaped belt; and
    a constricting device operable with the one or more pads and the C-shaped belt to compress each of the one or more pads onto a torso of a user with a compression force sufficient for decreasing a stretching of tendons and ligaments surrounding a uterus, thus relaxing the tissue and alleviating menstrual cramping.

11. An apparatus to relieve menstrual cramping according to claim 10, wherein each of the one or more pads has a left tapered portion and a right tapered portion.

12. An apparatus to relieve menstrual cramping according to claim 10, wherein the left tapered portion and the right tapered portion are symmetrical to one another.

13. An apparatus to relieve menstrual cramping according to claim 10, wherein the outer side of each of the one or more pads is semi-rigid and each inner side is flexible and compressible.

14. An apparatus to relieve menstrual cramping, the apparatus comprising:
    a pad having an outer side and an inner side;
    a strap having a first end and a second end at an opposite portion thereof, the strap having an outer side and an inner side, wherein the strap is affixed at its inner side to the outer side of the pad;
    a fastener connected to the first end and the opposing second end of the strap; and
    a constricting device operable with the strap and the pad to create a compression force onto the pad, wherein the compression force is sufficient for decreasing a stretching of tendons and ligaments surrounding a uterus, thus relaxing tissue and alleviating menstrual cramping when the apparatus is secured to a torso of a user.

\* \* \* \* \*